US012589218B2

(12) United States Patent (10) Patent No.: US 12,589,218 B2

Legaspi et al. (45) Date of Patent: Mar. 31, 2026

(54) INTERMITTENT-CATHETER ASSEMBLY AND METHODS THEREOF

(71) Applicant: C. R. Bard, Inc., Franklin Lakes, NJ (US)

(72) Inventors: Ronald N. Legaspi, Alpharetta, GA (US); James David Hughett, Sr., Monroe, GA (US); Kyle Daw, Smyrna, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 354 days.

(21) Appl. No.: 18/019,464

(22) PCT Filed: Jul. 29, 2021

(86) PCT No.: PCT/US2021/043771

§ 371 (c)(1),
(2) Date: Feb. 2, 2023

(87) PCT Pub. No.: WO2022/031520

PCT Pub. Date: Feb. 10, 2022

(65) Prior Publication Data

US 2023/0293848 A1 Sep. 21, 2023

Related U.S. Application Data

(60) Provisional application No. 63/211,922, filed on Jun. 17, 2021, provisional application No. 63/060,615, filed on Aug. 3, 2020.

(51) Int. Cl.
A61M 25/00 (2006.01)
A61M 25/04 (2006.01)

(52) U.S. Cl.
CPC ........ A61M 25/0017 (2013.01); A61M 25/04 (2013.01)

(58) Field of Classification Search
CPC ............ A61M 25/002; A61M 25/0017; A61M 25/0111; A61M 2210/1089;
(Continued)

(56) References Cited

U.S. PATENT DOCUMENTS

| 426,931 A | 4/1890 | Flower |
| 734,498 A | 7/1903 | Bachler |

(Continued)

FOREIGN PATENT DOCUMENTS

| AU | 2016283336 A1 | 12/2017 |
| AU | 2014362360 B2 | 1/2020 |

(Continued)

OTHER PUBLICATIONS

"Medifilm." Datasheet [online]. Mylan Technologies Inc., 2003 [retrieved on Febuary 14, 2020]. Retrieved from the Internet: <URL: https://web.archive.org/web/20030205090818/http://www.mylantech.com/products/medifilm.html>.

(Continued)

*Primary Examiner* — Adam Marcetich

(74) *Attorney, Agent, or Firm* — Rutan & Tucker LLP

(57) ABSTRACT

Disclosed herein are intermittent-catheter assemblies and methods thereof. An intermittent-catheter assembly includes, in some embodiments, a collapsible catheter housing and an intermittent catheter. The catheter housing can include an inner sleeve and an outer sleeve slidably mounted over the inner sleeve. Alternatively, the catheter housing can include an outer sleeve and a collapsible outer cover coupled to the outer sleeve. The intermittent catheter includes a funnel and a catheter tube coupled to the funnel. The intermittent-catheter assembly has a storage state and an opened state. In the storage state, the intermittent catheter is sealed within the catheter housing. In the opened state, the catheter housing is collapsed exposing the funnel of the (Continued)

intermittent catheter for removal of the intermittent catheter from the catheter housing. Methods of the intermittent-catheter assemblies include a method of using an intermittent-catheter assembly.

18 Claims, 8 Drawing Sheets

(58) Field of Classification Search
CPC .. A61M 2025/0175; A61M 2210/1085; A61M 25/01; A61M 2025/0681; A61M 2202/0496; A61M 2210/1092; A61M 2210/1096; A61M 25/0097; A61M 25/0113; B65D 43/162; B65D 83/0835; B65D 21/086; B65D 41/48; B65D 5/38; B65D 5/4279; B65D 5/721; B65D 5/723; A61B 2050/3006; A61B 50/30; A61F 2/0095
See application file for complete search history.

(56) References Cited

U.S. PATENT DOCUMENTS

| | | | |
|---|---|---|---|
| 1,131,865 A | 3/1915 | Putnam et al. |
| 1,235,142 A | 7/1917 | Ichilian |
| 1,304,396 A | 5/1919 | Smith |
| 1,643,289 A | 9/1927 | Emile |
| 1,661,494 A | 3/1928 | Nielsen |
| 1,876,229 A | 9/1932 | Oliver et al. |
| 1,888,349 A | 11/1932 | Jacoby |
| 1,978,497 A | 10/1934 | Lind |
| 2,043,630 A | 6/1936 | Raiche |
| 2,213,210 A | 9/1940 | Egbert |
| 2,228,992 A | 1/1941 | Fry |
| 2,230,226 A | 2/1941 | Auzin |
| 2,248,934 A | 7/1941 | Auzin |
| 2,262,749 A | 11/1941 | Berwald |
| 2,285,502 A | 6/1942 | Dreyfus |
| 2,308,484 A | 1/1943 | Auzin et al. |
| 2,314,262 A | 3/1943 | Winder |
| 2,320,157 A | 5/1943 | Raiche |
| 2,322,858 A | 6/1943 | Limbert et al. |
| 2,330,399 A | 9/1943 | Winder |
| 2,330,400 A | 9/1943 | Winder |
| 2,389,831 A | 11/1945 | Welsh |
| 2,390,070 A | 12/1945 | Auzin |
| 2,481,488 A | 9/1949 | Auzin |
| 2,494,393 A | 1/1950 | Lamson |
| 2,610,626 A | 9/1952 | Edwards |
| 2,638,093 A | 5/1953 | Kulick |
| 2,648,463 A | 8/1953 | Scherer |
| 2,649,619 A | 8/1953 | Killian |
| 2,649,854 A | 8/1953 | Salm |
| 2,690,595 A | 10/1954 | Raiche |
| 2,712,161 A | 7/1955 | Moss |
| 2,856,932 A | 10/1958 | Griffitts |
| 2,912,981 A | 11/1959 | Keough |
| 2,919,697 A | 1/1960 | Kim |
| 3,035,691 A | 5/1962 | Kai et al. |
| 3,044,468 A | 7/1962 | Birtwell |
| 3,053,257 A | 9/1962 | Birtwell |
| 3,076,464 A | 2/1963 | Rosenberg |
| 3,169,527 A | 2/1965 | Sheridan |
| 3,173,566 A | 3/1965 | Talbert |
| 3,211,151 A | 10/1965 | Foderick et al. |
| 3,246,075 A | 4/1966 | Dansard |
| 3,249,285 A | 5/1966 | Franz et al. |
| 3,304,353 A | 2/1967 | Harautuneian |
| 3,344,791 A | 10/1967 | Foderick |
| 3,345,988 A | 10/1967 | Vitello |
| 3,394,704 A | 7/1968 | Dery |
| 3,394,705 A | 7/1968 | Abramson |
| 3,403,682 A | 10/1968 | McDonell |
| 3,409,016 A | 11/1968 | Foley |
| 3,434,869 A | 3/1969 | Davidson |
| 3,463,141 A | 8/1969 | Mozolf |
| 3,478,743 A | 11/1969 | Ericson |
| 3,503,400 A | 3/1970 | Osthagen |
| 3,508,959 A | 4/1970 | Krahnke |
| 3,509,884 A | 5/1970 | Bell |
| 3,520,305 A | 7/1970 | Davis |
| 3,539,674 A | 11/1970 | Dereniuk et al. |
| 3,544,668 A | 12/1970 | Dereniuk |
| 3,548,805 A | 12/1970 | Datsenko |
| 3,556,294 A | 1/1971 | Walck et al. |
| 3,556,874 A | 1/1971 | McClain |
| 3,566,874 A | 3/1971 | Shepherd et al. |
| 3,593,713 A | 7/1971 | Bogoff et al. |
| 3,598,127 A | 8/1971 | Wepsic |
| 3,606,889 A | 9/1971 | Arblaster |
| 3,642,004 A | 2/1972 | Osthagen et al. |
| 3,646,929 A | 3/1972 | Bonnar |
| 3,648,704 A | 3/1972 | Jackson |
| 3,648,891 A | 3/1972 | Katz et al. |
| 3,651,615 A | 3/1972 | Bohner et al. |
| 3,683,928 A | 8/1972 | Kuntz |
| 3,695,921 A | 10/1972 | Shepherd et al. |
| 3,699,956 A | 10/1972 | Kitrilakis et al. |
| 3,699,964 A | 10/1972 | Ericson |
| 3,708,324 A | 1/1973 | Stebleton |
| 3,726,281 A | 4/1973 | Norton et al. |
| 3,739,783 A | 6/1973 | Broerman |
| 3,761,013 A | 9/1973 | Schuster |
| 3,762,399 A | 10/1973 | Riedell |
| 3,768,102 A | 10/1973 | Kwan-Gett et al. |
| 3,788,324 A | 1/1974 | Lim |
| 3,794,042 A | 2/1974 | De Klotz et al. |
| 3,797,478 A | 3/1974 | Walsh et al. |
| 3,802,987 A | 4/1974 | Noll |
| 3,835,992 A | 9/1974 | Adams, IV |
| 3,838,728 A | 10/1974 | Voegele |
| 3,841,304 A | 10/1974 | Jones |
| 3,854,483 A | 12/1974 | Powers |
| 3,861,395 A | 1/1975 | Taniguchi |
| 3,875,937 A | 4/1975 | Schmitt et al. |
| 3,879,516 A | 4/1975 | Wolvek |
| 3,882,220 A | 5/1975 | Ryder |
| 3,889,685 A | 6/1975 | Miller, Jr. et al. |
| 3,894,540 A | 7/1975 | Bonner, Jr. |
| 3,898,993 A | 8/1975 | Taniguchi |
| 3,924,634 A | 12/1975 | Taylor et al. |
| 3,926,309 A | 12/1975 | Center |
| 3,926,705 A | 12/1975 | Todd |
| 3,930,580 A | 1/1976 | Bazell et al. |
| 3,934,721 A | 1/1976 | Juster et al. |
| 3,962,519 A | 6/1976 | Rusch et al. |
| 3,967,728 A | 7/1976 | Gordon et al. |
| 3,981,299 A | 9/1976 | Murray |
| 3,983,879 A | 10/1976 | Todd |
| 4,026,296 A | 5/1977 | Stoy et al. |
| 4,029,104 A | 6/1977 | Kerber |
| 4,051,849 A | 10/1977 | Poncy et al. |
| 4,055,682 A | 10/1977 | Merrill |
| 4,062,363 A | 12/1977 | Bonner, Jr. |
| 4,069,359 A | 1/1978 | DeMarse et al. |
| 4,091,922 A | 5/1978 | Egler |
| 4,119,094 A | 10/1978 | Micklus et al. |
| 4,120,715 A | 10/1978 | Ockwell et al. |
| 4,133,303 A | 1/1979 | Patel |
| 4,140,127 A | 2/1979 | Cianci et al. |
| 4,149,539 A | 4/1979 | Cianci |
| 4,168,699 A | 9/1979 | Hauser |
| 4,170,996 A | 10/1979 | Wu |
| 4,186,745 A | 2/1980 | Lewis et al. |
| 4,187,851 A | 2/1980 | Hauser |
| 4,196,731 A | 4/1980 | Laurin et al. |
| 4,198,983 A | 4/1980 | Becker et al. |
| 4,198,984 A | 4/1980 | Taylor |
| 4,209,010 A | 6/1980 | Ward et al. |
| 4,225,371 A | 9/1980 | Taylor et al. |
| 4,230,115 A | 10/1980 | Walz, Jr. et al. |
| 4,245,639 A | 1/1981 | La Rosa |
| 4,246,909 A | 1/1981 | Wu et al. |

(56) References Cited

U.S. PATENT DOCUMENTS

| | | | |
|---|---|---|---|
| 4,249,535 | A | 2/1981 | Hargest, III |
| 4,252,760 | A | 2/1981 | Foster et al. |
| 4,265,848 | A | 5/1981 | Rusch |
| 4,266,999 | A | 5/1981 | Baier |
| 4,269,310 | A | 5/1981 | Uson |
| 4,284,459 | A | 8/1981 | Patel et al. |
| 4,287,227 | A | 9/1981 | Kamada et al. |
| 4,306,557 | A | 12/1981 | North |
| 4,311,146 | A | 1/1982 | Wonder |
| 4,311,659 | A | 1/1982 | Rey et al. |
| 4,318,406 | A | 3/1982 | McLeod |
| 4,318,947 | A | 3/1982 | Joung |
| 4,341,817 | A | 7/1982 | Tozier et al. |
| 4,343,788 | A | 8/1982 | Mustacich et al. |
| 4,350,161 | A | 9/1982 | Davis, Jr. |
| 4,351,333 | A | 9/1982 | Lazarus et al. |
| 4,366,901 | A | 1/1983 | Short |
| 4,367,732 | A | 1/1983 | Poulsen et al. |
| 4,378,018 | A | 3/1983 | Alexander et al. |
| 4,378,796 | A | 4/1983 | Milhaud |
| 4,379,506 | A | 4/1983 | Davidson |
| 4,381,008 | A | 4/1983 | Thomas et al. |
| 4,381,380 | A | 4/1983 | LeVeen et al. |
| 4,392,848 | A | 7/1983 | Lucas et al. |
| 4,395,806 | A | 8/1983 | Wonder et al. |
| 4,411,648 | A | 10/1983 | Davis et al. |
| 4,419,097 | A | 12/1983 | Rowland |
| 4,428,365 | A | 1/1984 | Hakky |
| 4,449,971 | A | 5/1984 | Cawood |
| 4,457,299 | A | 7/1984 | Cornwell |
| 4,472,226 | A | 9/1984 | Redinger et al. |
| 4,475,910 | A | 10/1984 | Conway et al. |
| 4,477,325 | A | 10/1984 | Osburn |
| 4,479,795 | A | 10/1984 | Mustacich et al. |
| 4,486,504 | A | 12/1984 | Chung |
| 4,496,354 | A | 1/1985 | Steer et al. |
| 4,515,593 | A | 5/1985 | Norton |
| 4,517,971 | A | 5/1985 | Sorbonne |
| 4,534,768 | A | 8/1985 | Osburn et al. |
| 4,539,234 | A | 9/1985 | Sakamoto et al. |
| 4,540,409 | A | 9/1985 | Nystrom et al. |
| 4,552,269 | A | 11/1985 | Chang |
| 4,553,533 | A | 11/1985 | Leighton |
| 4,560,382 | A | 12/1985 | Isono et al. |
| 4,563,184 | A | 1/1986 | Korol |
| 4,568,340 | A | 2/1986 | Giacalone |
| 4,571,239 | A | 2/1986 | Heyman |
| 4,571,240 | A | 2/1986 | Samson et al. |
| 4,571,241 | A | 2/1986 | Christopher |
| 4,576,599 | A | 3/1986 | Lipner |
| 4,581,026 | A | 4/1986 | Schneider |
| 4,581,028 | A | 4/1986 | Fox, Jr. et al. |
| 4,582,762 | A | 4/1986 | Onohara et al. |
| 4,585,666 | A | 4/1986 | Lambert |
| 4,586,974 | A | 5/1986 | Nystrom et al. |
| 4,589,874 | A | 5/1986 | Riedel et al. |
| 4,592,920 | A | 6/1986 | Murtfeldt |
| 4,597,765 | A | 7/1986 | Klatt |
| 4,597,931 | A | 7/1986 | Watanabe et al. |
| 4,601,713 | A | 7/1986 | Fuqua |
| 4,603,152 | A | 7/1986 | Laurin et al. |
| 4,607,746 | A | 8/1986 | Stinnette |
| 4,610,670 | A | 9/1986 | Spencer |
| 4,612,337 | A | 9/1986 | Fox, Jr. et al. |
| 4,613,324 | A | 9/1986 | Ghajar |
| 4,615,692 | A | 10/1986 | Giacalone et al. |
| 4,615,697 | A | 10/1986 | Robinson |
| 4,619,642 | A | 10/1986 | Spencer |
| 4,622,033 | A | 11/1986 | Taniguchi |
| 4,623,329 | A | 11/1986 | Drobish et al. |
| 4,626,250 | A | 12/1986 | Schneider |
| 4,627,844 | A | 12/1986 | Schmitt |
| 4,634,433 | A | 1/1987 | Osborne |
| 4,637,907 | A | 1/1987 | Hegel et al. |
| 4,638,790 | A | 1/1987 | Conway et al. |
| 4,639,246 | A | 1/1987 | Dudley |
| 4,640,688 | A | 2/1987 | Hauser |
| 4,652,259 | A | 3/1987 | O'Neil |
| 4,664,657 | A | 5/1987 | Williamitis et al. |
| 4,673,401 | A | 6/1987 | Jensen et al. |
| 4,677,143 | A | 6/1987 | Laurin et al. |
| 4,681,572 | A | 7/1987 | Tokarz et al. |
| 4,685,913 | A | 8/1987 | Austin |
| 4,686,124 | A | 8/1987 | Onohara et al. |
| 4,687,470 | A | 8/1987 | Okada |
| 4,692,152 | A | 9/1987 | Emde |
| 4,692,154 | A | 9/1987 | Singery et al. |
| 4,696,672 | A | 9/1987 | Mochizuki et al. |
| 4,699,616 | A | 10/1987 | Nowak et al. |
| 4,704,102 | A | 11/1987 | Guthery |
| 4,710,169 | A | 12/1987 | Christopher |
| 4,710,181 | A | 12/1987 | Fuqua |
| 4,723,946 | A | 2/1988 | Kay |
| 4,731,064 | A | 3/1988 | Heyden |
| 4,737,219 | A | 4/1988 | Taller et al. |
| 4,738,667 | A | 4/1988 | Galloway |
| 4,739,768 | A | 4/1988 | Engelson |
| 4,747,845 | A | 5/1988 | Korol |
| 4,754,877 | A | 7/1988 | Johansson et al. |
| 4,759,753 | A | 7/1988 | Schneider et al. |
| 4,762,128 | A | 8/1988 | Rosenbluth |
| 4,769,013 | A | 9/1988 | Lorenz et al. |
| 4,769,099 | A | 9/1988 | Therriault et al. |
| 4,772,473 | A | 9/1988 | Patel et al. |
| 4,773,901 | A | 9/1988 | Norton |
| 4,775,371 | A | 10/1988 | Mueller, Jr. |
| 4,784,651 | A | 11/1988 | Hickey et al. |
| 4,790,834 | A | 12/1988 | Austin |
| 4,790,835 | A | 12/1988 | Elias |
| D299,865 | S | 2/1989 | Kamstrup-Larsen et al. |
| 4,810,247 | A | 3/1989 | Glassman |
| 4,811,847 | A | 3/1989 | Reif et al. |
| 4,813,935 | A | 3/1989 | Haber et al. |
| 4,820,270 | A | 4/1989 | Hardcastle et al. |
| 4,820,289 | A | 4/1989 | Coury et al. |
| 4,820,291 | A | 4/1989 | Terauchi et al. |
| 4,820,292 | A | 4/1989 | Korol et al. |
| 4,834,721 | A | 5/1989 | Onohara et al. |
| 4,838,876 | A | 6/1989 | Wong et al. |
| 4,846,784 | A | 7/1989 | Haber |
| 4,846,909 | A | 7/1989 | Klug et al. |
| 4,850,969 | A | 7/1989 | Jackson |
| 4,861,337 | A | 8/1989 | George |
| 4,863,424 | A | 9/1989 | Blake, III et al. |
| 4,863,444 | A | 9/1989 | Blomer |
| 4,863,449 | A | 9/1989 | Therriault et al. |
| 4,867,748 | A | 9/1989 | Samuelsen |
| 4,874,373 | A | 10/1989 | Luther et al. |
| 4,876,109 | A | 10/1989 | Mayer et al. |
| 4,885,049 | A | 12/1989 | Johannesson |
| 4,886,508 | A | 12/1989 | Washington |
| 4,888,005 | A | 12/1989 | Dingeman et al. |
| 4,893,623 | A | 1/1990 | Rosenbluth |
| 4,894,059 | A | 1/1990 | Larsen et al. |
| 4,902,503 | A | 2/1990 | Umemura et al. |
| 4,904,260 | A | 2/1990 | Ray et al. |
| 4,917,113 | A | 4/1990 | Conway et al. |
| 4,917,686 | A | 4/1990 | Bayston et al. |
| RE33,206 | E | 5/1990 | Conway et al. |
| 4,923,450 | A | 5/1990 | Maeda et al. |
| 4,925,668 | A | 5/1990 | Khan et al. |
| 4,930,522 | A | 6/1990 | Busnel et al. |
| 4,931,056 | A | 6/1990 | Ghajar et al. |
| 4,932,938 | A | 6/1990 | Goldberg et al. |
| 4,932,948 | A | 6/1990 | Kernes et al. |
| 4,934,999 | A | 6/1990 | Bader |
| 4,935,260 | A | 6/1990 | Shlenker |
| 4,950,256 | A | 8/1990 | Luther et al. |
| 4,957,487 | A | 9/1990 | Gerow |
| 4,963,137 | A | 10/1990 | Heyden |
| 4,968,294 | A | 11/1990 | Salama |
| 4,968,507 | A | 11/1990 | Zentner et al. |
| 4,976,703 | A | 12/1990 | Franetzki et al. |
| 4,981,471 | A | 1/1991 | Quinn et al. |

(56) References Cited

U.S. PATENT DOCUMENTS

| | | |
|---|---|---|
| 4,994,047 A | 2/1991 | Walker et al. |
| 4,997,426 A | 3/1991 | Dingeman et al. |
| 5,004,454 A | 4/1991 | Beyar et al. |
| 5,007,897 A | 4/1991 | Kalb et al. |
| 5,013,306 A | 5/1991 | Solomon et al. |
| 5,013,717 A | 5/1991 | Solomon et al. |
| 5,019,096 A | 5/1991 | Fox, Jr. et al. |
| 5,019,378 A | 5/1991 | Allen |
| 5,019,601 A | 5/1991 | Allen |
| 5,045,078 A | 9/1991 | Asta |
| 5,059,190 A | 10/1991 | Novak |
| 5,071,406 A | 12/1991 | Jang |
| 5,077,352 A | 12/1991 | Elton |
| 5,078,707 A | 1/1992 | Peter Klug |
| 5,082,006 A | 1/1992 | Jonasson |
| 5,084,037 A | 1/1992 | Barnett |
| 5,087,252 A | 2/1992 | Denard |
| 5,088,980 A | 2/1992 | Leighton |
| 5,089,205 A | 2/1992 | Huang et al. |
| 5,090,424 A | 2/1992 | Simon et al. |
| 5,098,379 A | 3/1992 | Conway et al. |
| 5,100,396 A | 3/1992 | Zamierowski |
| 5,102,401 A | 4/1992 | Lambert et al. |
| 5,102,405 A | 4/1992 | Conway et al. |
| 5,109,378 A | 4/1992 | Proctor et al. |
| 5,109,601 A | 5/1992 | McBride |
| 5,112,306 A | 5/1992 | Burton et al. |
| 5,114,398 A | 5/1992 | Trick et al. |
| 5,118,007 A | 6/1992 | Lewis et al. |
| 5,128,088 A | 7/1992 | Shimomura et al. |
| 5,131,906 A | 7/1992 | Chen |
| 5,137,671 A | 8/1992 | Conway et al. |
| 5,140,999 A | 8/1992 | Ardito |
| 5,147,341 A | 9/1992 | Starke et al. |
| 5,165,952 A | 11/1992 | Solomon et al. |
| 5,174,290 A | 12/1992 | Fiddian-Green |
| 5,176,666 A | 1/1993 | Conway et al. |
| 5,179,174 A | 1/1993 | Elton |
| 5,180,591 A | 1/1993 | Magruder et al. |
| 5,186,172 A | 2/1993 | Fiddian-Green |
| 5,188,596 A | 2/1993 | Condon et al. |
| 5,197,957 A | 3/1993 | Wendler |
| 5,201,724 A | 4/1993 | Hukins et al. |
| 5,209,726 A | 5/1993 | Goosen |
| 5,209,728 A | 5/1993 | Kraus et al. |
| 5,211,640 A | 5/1993 | Wendler |
| 5,224,953 A | 7/1993 | Morgentaler |
| 5,226,530 A | 7/1993 | Golden |
| 5,234,411 A | 8/1993 | Vaillancourt et al. |
| 5,236,422 A | 8/1993 | Eplett, Jr. |
| 5,242,391 A | 9/1993 | Place et al. |
| 5,242,398 A | 9/1993 | Knoll et al. |
| 5,242,428 A | 9/1993 | Palestrant |
| 5,261,896 A | 11/1993 | Conway et al. |
| 5,263,947 A | 11/1993 | Kay |
| 5,269,755 A | 12/1993 | Bodicky |
| 5,269,770 A | 12/1993 | Conway et al. |
| 5,270,358 A | 12/1993 | Asmus |
| 5,282,795 A | 2/1994 | Finney |
| 5,290,306 A | 3/1994 | Trotta et al. |
| 5,306,226 A | 4/1994 | Salama |
| 5,334,175 A | 8/1994 | Conway et al. |
| 5,336,211 A | 8/1994 | Metz |
| 5,346,483 A | 9/1994 | Thaxton, Sr. |
| 5,348,536 A | 9/1994 | Young et al. |
| 5,352,182 A | 10/1994 | Kalb et al. |
| 5,354,132 A | 10/1994 | Young et al. |
| 5,360,402 A | 11/1994 | Conway et al. |
| 5,360,414 A | 11/1994 | Yarger |
| 5,366,449 A | 11/1994 | Gilberg |
| 5,368,575 A | 11/1994 | Chang |
| 5,370,899 A | 12/1994 | Conway et al. |
| 5,376,085 A | 12/1994 | Conway et al. |
| 5,380,312 A | 1/1995 | Goulter |
| 5,395,333 A | 3/1995 | Brill |
| 5,409,014 A | 4/1995 | Napoli et al. |
| 5,409,495 A | 4/1995 | Osborn |
| 5,415,165 A | 5/1995 | Fiddian-Green |
| 5,415,635 A | 5/1995 | Bagaoisan et al. |
| 5,417,226 A | 5/1995 | Juma |
| 5,417,666 A | 5/1995 | Coulter |
| 5,423,784 A | 6/1995 | Metz |
| 5,433,705 A | 7/1995 | Giebel et al. |
| 5,433,713 A | 7/1995 | Trotta |
| 5,445,626 A | 8/1995 | Gigante et al. |
| 5,447,231 A | 9/1995 | Kastenhofer |
| 5,451,424 A | 9/1995 | Solomon et al. |
| 5,454,798 A | 10/1995 | Kubalak et al. |
| 5,456,251 A | 10/1995 | Fiddian-Green |
| 5,464,650 A | 11/1995 | Berg et al. |
| 5,466,229 A | 11/1995 | Elson et al. |
| 5,476,434 A | 12/1995 | Kalb et al. |
| 5,479,945 A | 1/1996 | Simon |
| 5,482,740 A | 1/1996 | Conway et al. |
| 5,483,976 A | 1/1996 | McLaughlin et al. |
| 5,497,601 A | 3/1996 | Gonzalez |
| 5,501,669 A | 3/1996 | Conway et al. |
| 5,509,427 A | 4/1996 | Simon et al. |
| 5,509,889 A | 4/1996 | Kalb et al. |
| 5,509,899 A | 4/1996 | Fan et al. |
| 5,513,659 A | 5/1996 | Buuck et al. |
| 5,513,660 A | 5/1996 | Simon et al. |
| 5,514,112 A | 5/1996 | Chu et al. |
| 5,520,636 A | 5/1996 | Korth et al. |
| 5,531,715 A | 7/1996 | Engelson et al. |
| 5,531,717 A | 7/1996 | Roberto et al. |
| 5,536,258 A | 7/1996 | Folden |
| 5,538,584 A | 7/1996 | Metz |
| 5,554,140 A | 9/1996 | Michels et al. |
| 5,554,141 A | 9/1996 | Wendler |
| 5,558,900 A | 9/1996 | Fan et al. |
| 5,562,599 A | 10/1996 | Beyschlag |
| 5,567,495 A | 10/1996 | Modak et al. |
| 5,569,219 A | 10/1996 | Hakki et al. |
| 5,582,599 A | 12/1996 | Daneshvar |
| 5,591,292 A | 1/1997 | Blomqvist |
| 5,593,718 A | 1/1997 | Conway et al. |
| 5,599,321 A | 2/1997 | Conway et al. |
| 5,601,537 A | 2/1997 | Frassica |
| 5,607,417 A | 3/1997 | Batich et al. |
| 5,614,143 A | 3/1997 | Hager |
| 5,616,126 A | 4/1997 | Malekmehr et al. |
| 5,620,109 A | 4/1997 | Madden |
| 5,624,395 A | 4/1997 | Mikhail et al. |
| 5,630,429 A | 5/1997 | Dann |
| 5,643,235 A | 7/1997 | Figuerido |
| 5,645,048 A | 7/1997 | Brodsky et al. |
| 5,653,700 A | 8/1997 | Byrne et al. |
| 5,670,111 A | 9/1997 | Conway et al. |
| 5,671,755 A | 9/1997 | Simon et al. |
| 5,688,516 A | 11/1997 | Raad et al. |
| 5,695,456 A | 12/1997 | Cartmell et al. |
| 5,695,485 A | 12/1997 | Duperret et al. |
| 5,702,381 A | 12/1997 | Cottenden |
| 5,704,353 A | 1/1998 | Kalb et al. |
| 5,707,357 A | 1/1998 | Mikhail et al. |
| 5,709,672 A | 1/1998 | Ilner |
| 5,711,841 A | 1/1998 | Jaker |
| 5,724,994 A | 3/1998 | Simon et al. |
| 5,730,733 A | 3/1998 | Mortier et al. |
| 5,736,152 A | 4/1998 | Dunn |
| 5,749,826 A | 5/1998 | Faulkner |
| 5,752,525 A | 5/1998 | Simon et al. |
| 5,756,144 A | 5/1998 | Wolff et al. |
| 5,762,996 A | 6/1998 | Lucas et al. |
| 5,779,670 A | 7/1998 | Bidwell et al. |
| 5,782,808 A | 7/1998 | Folden |
| 5,785,694 A | 7/1998 | Cohen et al. |
| 5,788,687 A | 8/1998 | Batich et al. |
| 5,789,018 A | 8/1998 | Engelson et al. |
| 5,795,332 A | 8/1998 | Lucas et al. |
| 5,795,334 A | 8/1998 | Cochrane, III |
| 5,795,524 A | 8/1998 | Basso, Jr. et al. |
| 5,800,339 A | 9/1998 | Salama |

(56)                 References Cited

U.S. PATENT DOCUMENTS

| | | | |
|---|---|---|---|
| 5,806,527 A | 9/1998 | Borodulin et al. |
| 5,810,789 A | 9/1998 | Powers et al. |
| 5,817,067 A | 10/1998 | Tsukada et al. |
| 5,820,583 A | 10/1998 | Demopulos et al. |
| 5,820,607 A | 10/1998 | Tcholakian et al. |
| 5,827,247 A | 10/1998 | Kay |
| 5,827,249 A | 10/1998 | Jensen |
| 5,830,932 A | 11/1998 | Kay |
| 5,840,151 A | 11/1998 | Munsch |
| 5,848,691 A | 12/1998 | Morris et al. |
| 5,853,518 A | 12/1998 | Utas |
| 5,871,475 A | 2/1999 | Frassica |
| 5,877,243 A | 3/1999 | Sarangapani |
| 5,895,374 A | 4/1999 | Rodsten |
| 5,897,535 A | 4/1999 | Feliziani et al. |
| 5,902,631 A | 5/1999 | Wang et al. |
| 5,906,575 A | 5/1999 | Conway et al. |
| 5,919,170 A | 7/1999 | Woessner |
| 5,941,856 A | 8/1999 | Kovacs et al. |
| 5,958,167 A | 9/1999 | Van Driel et al. |
| 5,971,954 A | 10/1999 | Conway et al. |
| 5,980,483 A | 11/1999 | Dimitri |
| 5,980,507 A | 11/1999 | Fassuliotis et al. |
| 5,989,230 A | 11/1999 | Frassica |
| 5,997,517 A | 12/1999 | Whitbourne |
| 6,004,305 A | 12/1999 | Hursman et al. |
| 6,007,521 A | 12/1999 | Bidwell et al. |
| 6,007,524 A | 12/1999 | Schneider |
| 6,007,526 A | 12/1999 | Passalaqua et al. |
| 6,024,751 A | 2/2000 | Lovato et al. |
| 6,050,934 A | 4/2000 | Mikhail et al. |
| 6,053,905 A | 4/2000 | Daignault, Jr. et al. |
| 6,056,715 A | 5/2000 | Demopulos et al. |
| 6,059,107 A | 5/2000 | Nosted et al. |
| 6,063,063 A | 5/2000 | Harboe et al. |
| 6,065,597 A | 5/2000 | Pettersson et al. |
| 6,070,275 A | 6/2000 | Garlock |
| 6,090,075 A | 7/2000 | House |
| 6,097,976 A | 8/2000 | Yang et al. |
| 6,102,929 A | 8/2000 | Conway et al. |
| 6,113,582 A | 9/2000 | Dwork |
| 6,119,697 A | 9/2000 | Engel et al. |
| 6,131,575 A | 10/2000 | Lenker et al. |
| 6,132,399 A | 10/2000 | Shultz |
| 6,156,049 A | 12/2000 | Lovato et al. |
| 6,162,201 A | 12/2000 | Cohen et al. |
| 6,183,461 B1 | 2/2001 | Matsuura et al. |
| 6,186,990 B1 | 2/2001 | Chen et al. |
| 6,190,353 B1 | 2/2001 | Makower et al. |
| 6,206,885 B1 | 3/2001 | Ghahremani et al. |
| 6,210,394 B1 | 4/2001 | Demopulos et al. |
| 6,217,569 B1 | 4/2001 | Fiore |
| 6,221,056 B1 | 4/2001 | Silverman |
| 6,231,501 B1 | 5/2001 | Ditter |
| 6,238,383 B1 | 5/2001 | Karram et al. |
| 6,254,570 B1 | 7/2001 | Rutner et al. |
| 6,254,582 B1 | 7/2001 | O'Donnell et al. |
| 6,254,585 B1 | 7/2001 | Demopulos et al. |
| 6,256,525 B1 | 7/2001 | Yang et al. |
| 6,261,255 B1 | 7/2001 | Mullis et al. |
| 6,261,271 B1 | 7/2001 | Solomon et al. |
| 6,261,279 B1 | 7/2001 | Demopulos et al. |
| 6,270,902 B1 | 8/2001 | Tedeschi et al. |
| 6,280,425 B1 | 8/2001 | Del Guercio |
| 6,287,285 B1 | 9/2001 | Michal et al. |
| 6,293,923 B1 | 9/2001 | Yachia et al. |
| 6,296,627 B1 | 10/2001 | Edwards |
| 6,299,598 B1 | 10/2001 | Bander |
| 6,306,176 B1 | 10/2001 | Whitbourne |
| 6,306,422 B1 | 10/2001 | Batich et al. |
| 6,309,104 B1 | 10/2001 | Koch et al. |
| 6,315,711 B1 | 11/2001 | Conway et al. |
| 6,329,488 B1 | 12/2001 | Terry et al. |
| 6,340,359 B1 | 1/2002 | Silverman |
| 6,340,465 B1 | 1/2002 | Hsu et al. |
| 6,355,004 B1 | 3/2002 | Pedersen et al. |
| 6,358,229 B1 | 3/2002 | Tihon |
| 6,368,315 B1 | 4/2002 | Gillis et al. |
| 6,368,317 B2 | 4/2002 | Chang |
| 6,379,334 B1 | 4/2002 | Frassica |
| 6,383,434 B2 | 5/2002 | Conway et al. |
| 6,387,080 B1 | 5/2002 | Rodsten |
| 6,391,010 B1 | 5/2002 | Wilcox |
| 6,391,014 B1 | 5/2002 | Silverman |
| 6,398,718 B1 | 6/2002 | Yachia et al. |
| 6,402,726 B1 | 6/2002 | Genese |
| 6,409,717 B1 | 6/2002 | Sraelsson et al. |
| 6,423,041 B1 | 7/2002 | Grant |
| 6,437,038 B1 | 8/2002 | Chen |
| 6,440,060 B1 | 8/2002 | Latour, Jr. |
| 6,458,867 B1 | 10/2002 | Wang et al. |
| 6,468,245 B2 | 10/2002 | Alexandersen |
| 6,479,000 B2 | 11/2002 | Conway et al. |
| 6,479,726 B1 | 11/2002 | Cole |
| 6,485,476 B1 | 11/2002 | von Dyck et al. |
| 6,509,319 B1 | 1/2003 | Raad et al. |
| 6,544,240 B1 | 4/2003 | Borodulin et al. |
| 6,551,293 B1 | 4/2003 | Mitchell |
| 6,558,369 B2 | 5/2003 | Rosenblum |
| 6,558,792 B1 | 5/2003 | Vaabengaard et al. |
| 6,558,798 B2 | 5/2003 | Zhong et al. |
| 6,578,709 B1 | 6/2003 | Kavanagh et al. |
| 6,579,539 B2 | 6/2003 | Lawson et al. |
| 6,582,401 B1 | 6/2003 | Windheuser et al. |
| 6,596,401 B1 | 7/2003 | Terry et al. |
| 6,602,244 B2 | 8/2003 | Kavanagh et al. |
| 6,613,014 B1 | 9/2003 | Chi |
| 6,613,342 B2 | 9/2003 | Aoki |
| 6,626,888 B1 | 9/2003 | Conway et al. |
| 6,629,969 B2 | 10/2003 | Chan et al. |
| 6,632,204 B2 | 10/2003 | Guldfeldt et al. |
| 6,634,498 B2 | 10/2003 | Kayerod et al. |
| 6,638,269 B2 | 10/2003 | Wilcox |
| 6,648,906 B2 | 11/2003 | Lasheras et al. |
| 6,659,937 B2 | 12/2003 | Polsky et al. |
| 6,682,555 B2 | 1/2004 | Cioanta et al. |
| 6,693,189 B2 | 2/2004 | Holt et al. |
| 6,695,831 B1 | 2/2004 | Tsukada et al. |
| 6,706,025 B2 | 3/2004 | Engelson et al. |
| 6,711,436 B1 | 3/2004 | Duhaylongsod |
| 6,716,895 B1 | 4/2004 | Terry |
| 6,719,709 B2 | 4/2004 | Whalen et al. |
| 6,723,350 B2 | 4/2004 | Burrell et al. |
| 6,730,113 B2 | 5/2004 | Eckhardt et al. |
| 6,733,474 B2 | 5/2004 | Kusleika |
| 6,736,805 B2 | 5/2004 | Israelsson et al. |
| 6,740,273 B2 | 5/2004 | Lee |
| 6,746,421 B2 | 6/2004 | Yachia et al. |
| 6,767,551 B2 | 7/2004 | McGhee et al. |
| 6,780,504 B2 | 8/2004 | Rupprecht et al. |
| 6,783,520 B1 | 8/2004 | Candray et al. |
| D496,266 S | 9/2004 | Nestenborg |
| 6,787,156 B1 | 9/2004 | Bar-Shalom |
| 6,797,743 B2 | 9/2004 | McDonald et al. |
| 6,824,532 B2 | 11/2004 | Gillis et al. |
| 6,835,183 B2 | 12/2004 | Lennox et al. |
| 6,835,410 B2 | 12/2004 | Chabrecek et al. |
| 6,840,379 B2 | 1/2005 | Franks-Farah et al. |
| 6,848,574 B1 | 2/2005 | Sraelsson et al. |
| 6,849,070 B1 | 2/2005 | Hansen et al. |
| 6,852,098 B2 | 2/2005 | Byrne |
| 6,852,105 B2 | 2/2005 | Bolmsjo et al. |
| D503,335 S | 3/2005 | Risberg et al. |
| 6,869,416 B2 | 3/2005 | Windheuser et al. |
| 6,872,195 B2 | 3/2005 | Modak et al. |
| 6,887,223 B2 | 5/2005 | Bisbee |
| 6,887,230 B2 | 5/2005 | Kubalak et al. |
| 6,889,740 B1 | 5/2005 | Globensky et al. |
| 6,918,924 B2 | 7/2005 | Lasheras et al. |
| 6,926,708 B1 | 8/2005 | Franks-Farah et al. |
| 6,939,339 B1 | 9/2005 | Axexandersen et al. |
| 6,939,554 B2 | 9/2005 | McDonald et al. |
| 6,941,171 B2 | 9/2005 | Mann et al. |
| 6,942,634 B2 | 9/2005 | Odland |

(56) References Cited

U.S. PATENT DOCUMENTS

| | | |
|---|---|---|
| 6,945,957 B2 | 9/2005 | Freyman |
| 6,949,598 B2 | 9/2005 | Terry |
| 6,951,902 B2 | 10/2005 | McDonald et al. |
| 6,972,040 B2 | 12/2005 | Rioux et al. |
| 7,001,370 B2 | 2/2006 | Kubalak et al. |
| 7,033,367 B2 | 4/2006 | Ghahremani et al. |
| 7,048,717 B1 | 5/2006 | Frassica |
| 7,059,330 B1 | 6/2006 | Makower et al. |
| 7,066,912 B2 | 6/2006 | Nestenborg et al. |
| 7,087,041 B2 | 8/2006 | von Dyck et al. |
| 7,087,048 B2 | 8/2006 | Israelsson et al. |
| 7,094,220 B2 | 8/2006 | Tanghoj et al. |
| 7,112,298 B2 | 9/2006 | Kampa et al. |
| 7,160,277 B2 | 1/2007 | Elson et al. |
| 7,166,092 B2 | 1/2007 | Elson et al. |
| 7,195,608 B2 | 3/2007 | Burnett |
| 7,204,940 B2 | 4/2007 | McDonald et al. |
| 7,211,275 B2 | 5/2007 | Ying et al. |
| 7,244,242 B2 | 7/2007 | Freyman |
| 7,250,043 B2 | 7/2007 | Chan et al. |
| 7,255,687 B2 | 8/2007 | Huang et al. |
| 7,270,647 B2 | 9/2007 | Karpowicz et al. |
| 7,294,117 B2 | 11/2007 | Provost-Tine et al. |
| 7,311,690 B2 | 12/2007 | Burnett |
| 7,311,698 B2 | 12/2007 | Tanghoj et al. |
| 7,329,412 B2 | 2/2008 | Modak et al. |
| 7,331,948 B2 | 2/2008 | Skarda |
| 7,334,679 B2 | 2/2008 | Givens, Jr. |
| 7,374,040 B2 | 5/2008 | Lee et al. |
| 7,380,658 B2 | 6/2008 | Murray et al. |
| 7,402,559 B2 | 7/2008 | Catania et al. |
| 7,445,812 B2 | 11/2008 | Schmidt et al. |
| 7,458,964 B2 | 12/2008 | Mosler et al. |
| 7,476,223 B2 | 1/2009 | McBride |
| 7,507,229 B2 | 3/2009 | Hewitt et al. |
| 7,517,343 B2 | 4/2009 | Tanghoj et al. |
| 7,537,589 B2 | 5/2009 | Tsukada et al. |
| 7,571,804 B2 | 8/2009 | Kjellmann Bruun et al. |
| 7,601,158 B2 | 10/2009 | House |
| 7,615,045 B2 | 11/2009 | Israelsson et al. |
| 7,628,784 B2 | 12/2009 | Diaz et al. |
| 7,632,256 B2 | 12/2009 | Mosler et al. |
| D609,819 S | 2/2010 | Tomes et al. |
| 7,662,146 B2 | 2/2010 | House |
| 7,670,331 B2 | 3/2010 | Tanghoej |
| 7,682,353 B2 | 3/2010 | Tanghoj et al. |
| 7,682,669 B1 | 3/2010 | Michal et al. |
| 7,691,091 B1 | 4/2010 | Baggett |
| 7,691,476 B2 | 4/2010 | Finley |
| 7,717,902 B2 | 5/2010 | Sauer |
| 7,749,529 B2 | 7/2010 | Ash et al. |
| 7,770,726 B2 | 8/2010 | Murray et al. |
| 7,770,728 B2 | 8/2010 | Kaem |
| 7,780,640 B1 | 8/2010 | Amador |
| 7,780,642 B2 | 8/2010 | Rasmussen et al. |
| 7,789,873 B2 | 9/2010 | Kubalak et al. |
| 7,820,734 B2 | 10/2010 | McGhee |
| 7,823,722 B2 | 11/2010 | Bezou et al. |
| 7,846,133 B2 | 12/2010 | Windheuser et al. |
| 7,867,220 B2 | 1/2011 | Tanghoj |
| 7,886,907 B2 | 2/2011 | Murray et al. |
| 7,896,857 B2 | 3/2011 | Kay et al. |
| 7,918,831 B2 | 4/2011 | House |
| 7,938,838 B2 | 5/2011 | House |
| 7,947,021 B2 | 5/2011 | Bourne et al. |
| 7,985,217 B2 | 7/2011 | Mosler et al. |
| 8,007,464 B2 | 8/2011 | Gellman |
| 8,011,505 B2 | 9/2011 | Murray et al. |
| 8,051,981 B2 | 11/2011 | Murray et al. |
| 8,052,673 B2 | 11/2011 | Nestenborg |
| 8,053,030 B2 | 11/2011 | Gilman |
| 8,066,693 B2 | 11/2011 | Tanghoj et al. |
| 8,127,922 B2 | 3/2012 | Nordholm et al. |
| 8,133,580 B2 | 3/2012 | Dias et al. |
| 8,163,327 B2 | 4/2012 | Finley |
| 8,177,774 B2 | 5/2012 | House |
| 8,181,778 B1 | 5/2012 | van Groningen et al. |
| 8,192,413 B2 | 6/2012 | Bjerregaard |
| 8,201,689 B2 | 6/2012 | Kaern |
| 8,205,745 B2 | 6/2012 | Murray et al. |
| 8,207,393 B2 | 6/2012 | Bach |
| 8,230,993 B2 | 7/2012 | Tanghoej |
| 8,267,919 B2 | 9/2012 | Utas et al. |
| 8,282,624 B2 | 10/2012 | Tanghoej et al. |
| 8,287,519 B2 | 10/2012 | Smith |
| 8,287,890 B2 | 10/2012 | Elton |
| 8,298,202 B2 | 10/2012 | McCray |
| 8,303,556 B2 | 11/2012 | White |
| 8,317,775 B2 | 11/2012 | House |
| 8,328,792 B2 | 12/2012 | Nishtala et al. |
| 8,356,457 B2 | 1/2013 | Murray et al. |
| 8,377,498 B2 | 2/2013 | Rindlav-Westling et al. |
| 8,377,559 B2 | 2/2013 | Gilman |
| 8,382,708 B2 | 2/2013 | Mayback et al. |
| 8,398,615 B2 | 3/2013 | Torstensen et al. |
| 8,409,171 B2 | 4/2013 | Hannon et al. |
| 8,454,569 B2 | 6/2013 | Kull-Osterlin et al. |
| 8,459,455 B2 | 6/2013 | Frojd |
| 8,475,434 B2 | 7/2013 | Frojd |
| 8,523,843 B2 | 9/2013 | Kavanagh et al. |
| 8,556,884 B2 | 10/2013 | Hong et al. |
| 8,608,718 B1 | 12/2013 | Patterson-Young |
| 8,668,683 B2 | 3/2014 | Golden |
| 8,720,685 B2 | 5/2014 | Murray et al. |
| 8,805,533 B2 | 8/2014 | Boggs, II et al. |
| 8,871,869 B2 | 10/2014 | Dias et al. |
| 8,888,747 B2 | 11/2014 | House |
| 8,919,553 B2 | 12/2014 | Murray et al. |
| 8,974,438 B2 | 3/2015 | Hong et al. |
| 8,998,882 B2 | 4/2015 | Knapp et al. |
| 9,033,149 B2 | 5/2015 | Terry |
| 9,072,862 B2 | 7/2015 | Murray et al. |
| 9,078,760 B2 | 7/2015 | Marshall |
| 9,108,020 B1 | 8/2015 | Feloney |
| 9,114,227 B2 | 8/2015 | Blanchard |
| 9,138,510 B2 | 9/2015 | Madsen |
| 9,144,659 B2 | 9/2015 | Tanghoj |
| 9,168,354 B2 | 10/2015 | Hannon et al. |
| 9,186,438 B2 | 11/2015 | Gravesen et al. |
| 9,192,506 B2 | 11/2015 | Tanghoej et al. |
| 9,192,740 B2 | 11/2015 | Frojd |
| 9,199,057 B2 | 12/2015 | Nielsen |
| 9,205,222 B2 | 12/2015 | Tanghoj |
| 9,220,866 B2 | 12/2015 | Van Groningen et al. |
| 9,289,575 B2 | 3/2016 | Dye |
| 9,314,585 B2 | 4/2016 | Nestenborg et al. |
| 9,345,855 B2 | 5/2016 | Young |
| 9,511,204 B2 | 12/2016 | Tanghøj |
| 9,561,889 B2 | 2/2017 | Dayrit et al. |
| 9,649,472 B2 | 5/2017 | Kearns et al. |
| 9,669,187 B2 | 6/2017 | Tjassens et al. |
| 9,687,628 B2 | 6/2017 | Paz |
| 9,694,113 B2 | 7/2017 | Knapp et al. |
| 9,694,157 B2 | 7/2017 | Palmer |
| 9,707,375 B2 | 7/2017 | Conway et al. |
| 9,731,093 B2 | 8/2017 | Terry |
| 9,775,965 B2 | 10/2017 | Tanghoej et al. |
| 9,801,979 B2 | 10/2017 | Utas et al. |
| 9,821,139 B2 | 11/2017 | Carleo |
| 9,872,969 B2 | 1/2018 | Conway et al. |
| 9,884,167 B2 | 2/2018 | Gustavsson |
| 9,918,869 B2 | 3/2018 | Henry et al. |
| 9,937,334 B2 | 4/2018 | Fröjd et al. |
| 10,112,031 B2 | 10/2018 | Matthiassen |
| 10,118,019 B2 | 11/2018 | Murray et al. |
| 10,149,961 B2 | 12/2018 | Carleo |
| 10,166,366 B2 | 1/2019 | Murray et al. |
| 10,179,676 B1 * | 1/2019 | Taylor .................. B65D 55/165 |
| 10,207,076 B2 | 2/2019 | Foley et al. |
| 10,265,499 B2 | 4/2019 | Hong et al. |
| 10,328,237 B2 | 6/2019 | Kelly et al. |
| 10,406,322 B2 | 9/2019 | O'Flynn et al. |
| 10,441,454 B2 | 10/2019 | Tanghoej et al. |
| 10,449,328 B2 | 10/2019 | Tanghoej et al. |

(56)  References Cited

U.S. PATENT DOCUMENTS

| | | | |
|---|---|---|---|
| 10,449,329 | B2 | 10/2019 | Foley et al. |
| 10,518,000 | B2 | 12/2019 | Knapp et al. |
| 10,561,817 | B2 | 2/2020 | Hannon et al. |
| 10,569,046 | B2 | 2/2020 | Steindahl et al. |
| 10,569,051 | B2 | 2/2020 | Conway et al. |
| 10,639,451 | B2 | 5/2020 | Kearns et al. |
| 10,646,688 | B2 | 5/2020 | Hannon et al. |
| 10,702,671 | B2 | 7/2020 | Terry |
| 10,758,704 | B2 | 9/2020 | Hickmott et al. |
| 10,765,833 | B2 | 9/2020 | Kearns |
| 10,857,324 | B2 | 12/2020 | Yin et al. |
| 10,874,825 | B2 | 12/2020 | Yin et al. |
| RE48,426 | E | 2/2021 | Murray et al. |
| 10,912,917 | B2 | 2/2021 | Terry |
| 11,020,561 | B2 | 6/2021 | O'Brien et al. |
| 11,103,676 | B2 | 8/2021 | McMenamin et al. |
| 11,129,961 | B2 | 9/2021 | O'Flynn |
| 11,141,562 | B2 | 10/2021 | McMenamin et al. |
| 11,154,688 | B2 | 10/2021 | Schertiger |
| 11,167,107 | B2 | 11/2021 | Schertiger et al. |
| 11,235,130 | B2 | 2/2022 | Murray et al. |
| 11,241,566 | B1 | 2/2022 | Lindsay |
| 11,253,675 | B2 | 2/2022 | Fletter |
| 11,344,702 | B2 | 5/2022 | Subramaniam et al. |
| 11,400,257 | B2 | 8/2022 | Tierney et al. |
| 11,420,017 | B2 | 8/2022 | Hilton et al. |
| 11,534,573 | B2 | 12/2022 | Hannon et al. |
| 11,547,833 | B2 | 1/2023 | Murray et al. |
| 11,607,524 | B2 | 3/2023 | Conway et al. |
| 12,383,700 | B2 | 8/2025 | Murray et al. |
| 2001/0001443 | A1 | 5/2001 | Kayerod et al. |
| 2001/0027299 | A1 | 10/2001 | Yang et al. |
| 2001/0031933 | A1 | 10/2001 | Cannon |
| 2001/0031952 | A1 | 10/2001 | Karram et al. |
| 2001/0047147 | A1 | 11/2001 | Slepian et al. |
| 2001/0054562 | A1 | 12/2001 | Pettersson et al. |
| 2002/0007175 | A1 | 1/2002 | Chang |
| 2002/0032406 | A1 | 3/2002 | Kusleika |
| 2002/0037943 | A1 | 3/2002 | Madsen |
| 2002/0045855 | A1 | 4/2002 | Frassica |
| 2002/0055730 | A1 | 5/2002 | Yachia et al. |
| 2002/0077611 | A1 | 6/2002 | von Dyck et al. |
| 2002/0082551 | A1 | 6/2002 | Yachia et al. |
| 2002/0087131 | A1 | 7/2002 | Wolff et al. |
| 2002/0094322 | A1 | 7/2002 | Lawson et al. |
| 2002/0095133 | A1 | 7/2002 | Gillis et al. |
| 2002/0099356 | A1 | 7/2002 | Unger et al. |
| 2002/0103467 | A1 | 8/2002 | Kubalak |
| 2002/0107467 | A1 | 8/2002 | Levin |
| 2002/0132013 | A1 | 9/2002 | Moulis |
| 2002/0132049 | A1 | 9/2002 | Leonard et al. |
| 2002/0133130 | A1 | 9/2002 | Wilcox |
| 2002/0156440 | A1 | 10/2002 | Israelsson et al. |
| 2002/0165427 | A1 | 11/2002 | Yachia et al. |
| 2002/0169438 | A1 | 11/2002 | Sauer |
| 2002/0182265 | A1 | 12/2002 | Burrell et al. |
| 2003/0004496 | A1 | 1/2003 | Tanghoj |
| 2003/0018293 | A1 | 1/2003 | Tanghoj et al. |
| 2003/0018302 | A1 | 1/2003 | Kavanagh et al. |
| 2003/0018322 | A1 | 1/2003 | Tanghoj et al. |
| 2003/0023222 | A1 | 1/2003 | Chen |
| 2003/0028174 | A1 | 2/2003 | Chan et al. |
| 2003/0036802 | A1 | 2/2003 | Lennox et al. |
| 2003/0055403 | A1 | 3/2003 | Nestenborg et al. |
| 2003/0060807 | A1 | 3/2003 | Tanghoj et al. |
| 2003/0065292 | A1 | 4/2003 | Darouiche et al. |
| 2003/0083644 | A1 | 5/2003 | Avaltroni |
| 2003/0130646 | A1 | 7/2003 | Kubalak et al. |
| 2003/0132307 | A1 | 7/2003 | Park |
| 2003/0135200 | A1 | 7/2003 | Byrne |
| 2003/0163079 | A1 | 8/2003 | Burnett |
| 2003/0168365 | A1 | 9/2003 | Kaem |
| 2003/0195478 | A1 | 10/2003 | Russo |
| 2003/0225392 | A1 | 12/2003 | McMichael et al. |
| 2003/0233084 | A1 | 12/2003 | Slepian et al. |
| 2004/0030301 | A1 | 2/2004 | Hunter |
| 2004/0034329 | A1 | 2/2004 | Mankus et al. |
| 2004/0044307 | A1 | 3/2004 | Richardson et al. |
| 2004/0049152 | A1 | 3/2004 | Nayak |
| 2004/0049170 | A1 | 3/2004 | Snell |
| 2004/0055925 | A1 | 3/2004 | Franks-Farah et al. |
| 2004/0059280 | A1 | 3/2004 | Makower et al. |
| 2004/0068251 | A1 | 4/2004 | Chan et al. |
| 2004/0074794 | A1 | 4/2004 | Conway et al. |
| 2004/0097892 | A1 | 5/2004 | Evans et al. |
| 2004/0116551 | A1 | 6/2004 | Terry |
| 2004/0122382 | A1 | 6/2004 | Johnson et al. |
| 2004/0127848 | A1 | 7/2004 | Freyman |
| 2004/0133156 | A1 | 7/2004 | Diaz et al. |
| 2004/0147871 | A1 | 7/2004 | Burnett |
| 2004/0153049 | A1 | 8/2004 | Hewitt et al. |
| 2004/0153051 | A1 | 8/2004 | Israelsson et al. |
| 2004/0158231 | A1 | 8/2004 | Tanghoj et al. |
| 2004/0163980 | A1 | 8/2004 | Tanghoj et al. |
| 2004/0176747 | A1 | 9/2004 | Feneley |
| 2004/0193143 | A1 | 9/2004 | Sauer |
| 2004/0234572 | A1 | 11/2004 | Martinod et al. |
| 2004/0236293 | A1 | 11/2004 | Tanghoj et al. |
| 2004/0243104 | A1 | 12/2004 | Seddon |
| 2004/0249343 | A1 | 12/2004 | Cioanta |
| 2004/0254562 | A1 | 12/2004 | Tanghoj et al. |
| 2004/0256264 | A1 | 12/2004 | Israelsson et al. |
| 2005/0003118 | A1 | 1/2005 | Takala |
| 2005/0011790 | A1* | 1/2005 | Harrold ............... B65D 50/061 |
| | | | 206/363 |
| 2005/0015076 | A1 | 1/2005 | Giebmeyer et al. |
| 2005/0031872 | A1 | 2/2005 | Schmidt et al. |
| 2005/0033222 | A1 | 2/2005 | Haggstrom et al. |
| 2005/0043715 | A1 | 2/2005 | Nestenborg et al. |
| 2005/0049577 | A1 | 3/2005 | Snell et al. |
| 2005/0059990 | A1 | 3/2005 | Ayala et al. |
| 2005/0065499 | A1 | 3/2005 | Douk et al. |
| 2005/0070882 | A1 | 3/2005 | McBride |
| 2005/0080399 | A1 | 4/2005 | Bolmsjo et al. |
| 2005/0096582 | A1 | 5/2005 | Burnett |
| 2005/0101923 | A1 | 5/2005 | Elson et al. |
| 2005/0101924 | A1 | 5/2005 | Elson et al. |
| 2005/0107735 | A1 | 5/2005 | Lennox et al. |
| 2005/0107771 | A1 | 5/2005 | Finkbeiner |
| 2005/0109648 | A1 | 5/2005 | Kerzman et al. |
| 2005/0137522 | A1 | 6/2005 | Aoki |
| 2005/0137582 | A1 | 6/2005 | Kull-Osterlin et al. |
| 2005/0143690 | A1 | 6/2005 | High |
| 2005/0148950 | A1 | 7/2005 | Windheuser et al. |
| 2005/0177104 | A1 | 8/2005 | Conway |
| 2005/0197531 | A1 | 9/2005 | Cabiri et al. |
| 2005/0199521 | A1 | 9/2005 | Givens |
| 2005/0209580 | A1 | 9/2005 | Freyman |
| 2005/0214443 | A1 | 9/2005 | Madsen |
| 2005/0245901 | A1 | 11/2005 | Floyd |
| 2005/0251108 | A1 | 11/2005 | Frassica |
| 2005/0256447 | A1 | 11/2005 | Richardson et al. |
| 2005/0273034 | A1 | 12/2005 | Burnett |
| 2005/0282977 | A1 | 12/2005 | Stempel et al. |
| 2005/0283136 | A1 | 12/2005 | Skarda |
| 2006/0025753 | A1 | 2/2006 | Kubalak et al. |
| 2006/0027854 | A1 | 2/2006 | Kim et al. |
| 2006/0030864 | A1 | 2/2006 | Kennedy, et al. |
| 2006/0036208 | A1 | 2/2006 | Burnett |
| 2006/0041246 | A1 | 2/2006 | Provost-tine et al. |
| 2006/0054557 | A1 | 3/2006 | Hori et al. |
| 2006/0058777 | A1 | 3/2006 | Nielsen |
| 2006/0064065 | A1 | 3/2006 | Russo |
| 2006/0079835 | A1 | 4/2006 | Frassica |
| 2006/0079854 | A1 | 4/2006 | Kay et al. |
| 2006/0100511 | A1 | 5/2006 | Eriksen |
| 2006/0122566 | A1 | 6/2006 | Huang et al. |
| 2006/0122568 | A1 | 6/2006 | Elson et al. |
| 2006/0142737 | A1 | 6/2006 | Tanghoj |
| 2006/0172096 | A1 | 8/2006 | Kyle et al. |
| 2006/0184112 | A1 | 8/2006 | Horn et al. |
| 2006/0184145 | A1 | 8/2006 | Ciok et al. |
| 2006/0189962 | A1 | 8/2006 | Burtoft |
| 2006/0196783 | A1 | 9/2006 | Bruun et al. |

(56) References Cited

U.S. PATENT DOCUMENTS

| | | |
|---|---|---|
| 2006/0200079 A1 | 9/2006 | Magnusson |
| 2006/0229576 A1 | 10/2006 | Conway et al. |
| 2006/0240069 A1 | 10/2006 | Utas et al. |
| 2006/0263404 A1 | 11/2006 | Nielsen et al. |
| 2006/0271019 A1 | 11/2006 | Stoller et al. |
| 2006/0276894 A1 | 12/2006 | Finley |
| 2006/0278546 A1 | 12/2006 | State et al. |
| 2006/0293642 A1 | 12/2006 | Israelsson et al. |
| 2007/0005024 A1 | 1/2007 | Weber et al. |
| 2007/0005041 A1 | 1/2007 | Frassica et al. |
| 2007/0010798 A1 | 1/2007 | Stoller et al. |
| 2007/0016168 A1 | 1/2007 | Conway |
| 2007/0016169 A1 | 1/2007 | Utas et al. |
| 2007/0049879 A1 | 3/2007 | Gutierrez |
| 2007/0059350 A1 | 3/2007 | Kennedy et al. |
| 2007/0066963 A1 | 3/2007 | Tanghoj |
| 2007/0084749 A1* | 4/2007 | Demelo ........... G01N 33/48778 |
| | | 206/569 |
| 2007/0088330 A1 | 4/2007 | House |
| 2007/0106233 A1 | 5/2007 | Huang et al. |
| 2007/0108076 A1* | 5/2007 | Miller .................... B25H 3/003 |
| | | 220/8 |
| 2007/0112327 A1 | 5/2007 | Yun et al. |
| 2007/0112333 A1 | 5/2007 | Hoang et al. |
| 2007/0149929 A1 | 6/2007 | Utas et al. |
| 2007/0161971 A1 | 7/2007 | House |
| 2007/0197957 A1 | 8/2007 | Hunter et al. |
| 2007/0218102 A1 | 9/2007 | Chudzik et al. |
| 2007/0225635 A1 | 9/2007 | Lynn |
| 2007/0225649 A1 | 9/2007 | House |
| 2007/0225687 A1 | 9/2007 | House |
| 2007/0244449 A1 | 10/2007 | Najafi et al. |
| 2007/0287800 A1 | 12/2007 | Acquarulo et al. |
| 2007/0289887 A1 | 12/2007 | Murray et al. |
| 2008/0006554 A1 | 1/2008 | Duffy et al. |
| 2008/0015518 A1 | 1/2008 | Huang et al. |
| 2008/0015527 A1 | 1/2008 | House |
| 2008/0021382 A1 | 1/2008 | Freyman |
| 2008/0027414 A1 | 1/2008 | Tanghoj et al. |
| 2008/0033471 A1 | 2/2008 | Paz et al. |
| 2008/0050446 A1 | 2/2008 | Ziegler et al. |
| 2008/0051762 A1 | 2/2008 | Tsukada et al. |
| 2008/0051763 A1 | 2/2008 | Frojd |
| 2008/0063324 A1 | 3/2008 | Bernard et al. |
| 2008/0077099 A1 | 3/2008 | House |
| 2008/0082051 A1 | 4/2008 | Miller et al. |
| 2008/0085949 A1 | 4/2008 | McGhee |
| 2008/0091145 A1 | 4/2008 | House |
| 2008/0097362 A1 | 4/2008 | Mosler et al. |
| 2008/0097394 A1 | 4/2008 | Lampropoulos et al. |
| 2008/0097411 A1 | 4/2008 | House |
| 2008/0103464 A1 | 5/2008 | Mosler et al. |
| 2008/0119803 A1 | 5/2008 | Lund |
| 2008/0125513 A1 | 5/2008 | Kristiansen |
| 2008/0140010 A1 | 6/2008 | Kennedy et al. |
| 2008/0140052 A1 | 6/2008 | Moller et al. |
| 2008/0171973 A1 | 7/2008 | House |
| 2008/0171998 A1 | 7/2008 | House |
| 2008/0172016 A1 | 7/2008 | House |
| 2008/0172040 A1 | 7/2008 | Smith |
| 2008/0172042 A1 | 7/2008 | House |
| 2008/0177217 A1 | 7/2008 | Polaschegg |
| 2008/0179208 A1 | 7/2008 | Murray et al. |
| 2008/0183262 A1 | 7/2008 | Dowling |
| 2008/0193497 A1 | 8/2008 | Samuelsen et al. |
| 2008/0200907 A1 | 8/2008 | Nestenborg |
| 2008/0215021 A1 | 9/2008 | Cisko, Jr. et al. |
| 2008/0243081 A1 | 10/2008 | Nance et al. |
| 2008/0243091 A1 | 10/2008 | Humphreys et al. |
| 2008/0249467 A1 | 10/2008 | Burnett et al. |
| 2008/0249482 A1 | 10/2008 | Erez |
| 2008/0275463 A1 | 11/2008 | High |
| 2008/0279907 A1 | 11/2008 | Ash et al. |
| 2008/0281291 A1 | 11/2008 | Tihon et al. |
| 2009/0000970 A1 | 1/2009 | Bordeau et al. |
| 2009/0005725 A1 | 1/2009 | Shorey |
| 2009/0012208 A1 | 1/2009 | Madsen et al. |
| 2009/0024111 A1 | 1/2009 | Borodulin et al. |
| 2009/0043287 A1 | 2/2009 | Mosler et al. |
| 2009/0048537 A1 | 2/2009 | Lydon et al. |
| 2009/0048570 A1 | 2/2009 | Jensen |
| 2009/0054876 A1 | 2/2009 | Borodulin et al. |
| 2009/0062754 A1 | 3/2009 | Tang |
| 2009/0065605 A1 | 3/2009 | Roche et al. |
| 2009/0071851 A1 | 3/2009 | Maki et al. |
| 2009/0099532 A1 | 4/2009 | Cuevas et al. |
| 2009/0101531 A1 | 4/2009 | Nordholm et al. |
| 2009/0112171 A1 | 4/2009 | Ng et al. |
| 2009/0131917 A1 | 5/2009 | Kavanagh et al. |
| 2009/0137985 A1 | 5/2009 | Tanghoej et al. |
| 2009/0137986 A1 | 5/2009 | Golden et al. |
| 2009/0149837 A1 | 6/2009 | Tanghoj et al. |
| 2009/0156882 A1 | 6/2009 | Chi Sing et al. |
| 2009/0163884 A1 | 6/2009 | Kull-Osterlin et al. |
| 2009/0200187 A1 | 8/2009 | Nestenborg et al. |
| 2009/0208368 A1 | 8/2009 | Waldrep et al. |
| 2009/0221992 A1 | 9/2009 | Hannon et al. |
| 2009/0299334 A1 | 12/2009 | Nishtala et al. |
| 2009/0314795 A1* | 12/2009 | Rapko .................... B25B 23/00 |
| | | 221/251 |
| 2009/0318900 A1 | 12/2009 | Tanghoj et al. |
| 2010/0010086 A1 | 1/2010 | Ash et al. |
| 2010/0030197 A1 | 2/2010 | House |
| 2010/0036363 A1 | 2/2010 | Watanabe et al. |
| 2010/0047123 A1 | 2/2010 | Solomon et al. |
| 2010/0086580 A1 | 4/2010 | Nyman et al. |
| 2010/0133172 A1 | 6/2010 | Song et al. |
| 2010/0152686 A1 | 6/2010 | Ryder et al. |
| 2010/0155268 A1 | 6/2010 | Murray et al. |
| 2010/0198195 A1 | 8/2010 | Nishtala et al. |
| 2010/0228233 A1 | 9/2010 | Kahn |
| 2010/0256576 A1 | 10/2010 | Aggarwal et al. |
| 2010/0258568 A1* | 10/2010 | Frederiksen ....... A61M 25/0111 |
| | | 53/474 |
| 2010/0263327 A1 | 10/2010 | Murray et al. |
| 2010/0324540 A1 | 12/2010 | Paulen et al. |
| 2011/0028943 A1 | 2/2011 | Lawson et al. |
| 2011/0056852 A1 | 3/2011 | Frojd |
| 2011/0059874 A1 | 3/2011 | Rooijmans et al. |
| 2011/0060317 A1 | 3/2011 | Frojd |
| 2011/0114520 A1 | 5/2011 | Matthison-Hansen |
| 2011/0127186 A1 | 6/2011 | Enns et al. |
| 2011/0137243 A1 | 6/2011 | Hossainy et al. |
| 2011/0137296 A1 | 6/2011 | Tanghoj |
| 2011/0144579 A1 | 6/2011 | Elton |
| 2011/0147238 A1 | 6/2011 | Tanghoej et al. |
| 2011/0152843 A1 | 6/2011 | Wedlin et al. |
| 2011/0160704 A1 | 6/2011 | Park |
| 2011/0178507 A1 | 7/2011 | Bracken et al. |
| 2011/0184386 A1 | 7/2011 | House |
| 2011/0213025 A1 | 9/2011 | Finch, Jr. |
| 2011/0224653 A1* | 9/2011 | Torstensen ........ A61M 25/0017 |
| | | 604/544 |
| 2011/0284409 A1 | 11/2011 | Murray et al. |
| 2011/0295239 A1 | 12/2011 | Gustavsson |
| 2012/0037525 A1 | 2/2012 | Peck et al. |
| 2012/0168324 A1 | 7/2012 | Carleo |
| 2012/0179102 A1 | 7/2012 | Blanchard et al. |
| 2012/0179144 A1 | 7/2012 | Carleo |
| 2012/0193255 A1 | 8/2012 | Lareau et al. |
| 2012/0219742 A1 | 8/2012 | Gravesen et al. |
| 2012/0228165 A1 | 9/2012 | Murray et al. |
| 2012/0239005 A1 | 9/2012 | Conway et al. |
| 2012/0271101 A1 | 10/2012 | Tan |
| 2012/0284991 A1 | 11/2012 | Kusz et al. |
| 2012/0308805 A1 | 12/2012 | Sella |
| 2012/0310210 A1 | 12/2012 | Campbell et al. |
| 2012/0316515 A1 | 12/2012 | Terry |
| 2012/0330255 A1 | 12/2012 | Carlin |
| 2013/0006226 A1 | 1/2013 | Hong et al. |
| 2013/0037306 A1 | 2/2013 | Kim |
| 2013/0048516 A1 | 2/2013 | Nishtala et al. |
| 2013/0077899 A1 | 3/2013 | Odabashian et al. |
| 2013/0085469 A1 | 4/2013 | Polaschegg |

(56) References Cited

U.S. PATENT DOCUMENTS

| | | | |
|---|---|---|---|
| 2013/0131647 A1 | 5/2013 | Nielsen | |
| 2013/0138083 A1 | 5/2013 | Tennican | |
| 2013/0138088 A1 | 5/2013 | Nielsen | |
| 2013/0146599 A1 | 6/2013 | Murray et al. | |
| 2013/0153446 A1 | 6/2013 | Utas et al. | |
| 2013/0161208 A1 | 6/2013 | Gustavsson | |
| 2013/0161227 A1 | 6/2013 | Gustavsson | |
| 2013/0186778 A1 | 7/2013 | Terry | |
| 2013/0218136 A1* | 8/2013 | Tanghoej | A61M 25/00 |
| | | | 604/544 |
| 2013/0231641 A1 | 9/2013 | Gustavsson | |
| 2013/0253426 A1 | 9/2013 | Campbell et al. | |
| 2013/0261608 A1 | 10/2013 | Tanghoj | |
| 2013/0264227 A1 | 10/2013 | Frojd | |
| 2013/0289537 A1* | 10/2013 | Schertiger | F16L 19/083 |
| | | | 604/544 |
| 2014/0066904 A1 | 3/2014 | Young | |
| 2014/0066905 A1 | 3/2014 | Young | |
| 2014/0193474 A1 | 7/2014 | Babcock et al. | |
| 2014/0194857 A1 | 7/2014 | Eilat | |
| 2014/0224678 A1 | 8/2014 | Schertiger et al. | |
| 2014/0262859 A1 | 9/2014 | Knapp et al. | |
| 2014/0271351 A1 | 9/2014 | Nielsen et al. | |
| 2014/0271400 A1* | 9/2014 | Cheng | B01L 3/5023 |
| | | | 422/417 |
| 2015/0001107 A1 | 1/2015 | Gustavsson | |
| 2015/0051587 A1 | 2/2015 | Rolsted et al. | |
| 2015/0068927 A1 | 3/2015 | McBurney et al. | |
| 2015/0105756 A1 | 4/2015 | O'Brien et al. | |
| 2015/0126975 A1 | 5/2015 | Wuthier | |
| 2015/0133898 A1 | 5/2015 | Murray et al. | |
| 2015/0202405 A1 | 7/2015 | Schertiger et al. | |
| 2015/0231377 A1 | 8/2015 | Tierney et al. | |
| 2015/0238726 A1 | 8/2015 | Terry | |
| 2015/0258305 A1 | 9/2015 | Dye | |
| 2015/0265801 A1 | 9/2015 | Rostami | |
| 2015/0273116 A1 | 10/2015 | Knapp et al. | |
| 2015/0273183 A1 | 10/2015 | Foley et al. | |
| 2015/0297861 A1 | 10/2015 | Passalaqua et al. | |
| 2015/0297862 A1 | 10/2015 | Sadik et al. | |
| 2015/0306342 A1 | 10/2015 | Rostami et al. | |
| 2015/0314103 A1 | 11/2015 | Hannon et al. | |
| 2015/0335854 A1 | 11/2015 | Dvarsater et al. | |
| 2015/0335856 A1 | 11/2015 | Utas et al. | |
| 2015/0335872 A1 | 11/2015 | Yang et al. | |
| 2015/0343171 A1 | 12/2015 | Hannon | |
| 2015/0352324 A1 | 12/2015 | Palmer | |
| 2015/0359996 A1 | 12/2015 | Arora et al. | |
| 2016/0001037 A1 | 1/2016 | Hong et al. | |
| 2016/0038652 A1 | 2/2016 | Gilman | |
| 2016/0038713 A1 | 2/2016 | Kearns et al. | |
| 2016/0120688 A1 | 5/2016 | Lee | |
| 2016/0166822 A1 | 6/2016 | Dodson et al. | |
| 2016/0175488 A1 | 6/2016 | Klein et al. | |
| 2016/0184551 A1 | 6/2016 | Nyman et al. | |
| 2016/0193447 A1* | 7/2016 | Matthiassen | A61M 25/0136 |
| | | | 604/544 |
| 2016/0220784 A1 | 8/2016 | Palmer | |
| 2016/0317715 A1 | 11/2016 | Rostami et al. | |
| 2016/0325088 A1 | 11/2016 | Nordquist et al. | |
| 2016/0325089 A1 | 11/2016 | Burkholz | |
| 2017/0173300 A1 | 6/2017 | Hannon et al. | |
| 2017/0217658 A1 | 8/2017 | Whitehurst | |
| 2017/0296704 A1 | 10/2017 | Knapp et al. | |
| 2017/0326334 A1 | 11/2017 | Terry | |
| 2018/0021481 A1 | 1/2018 | Yin et al. | |
| 2018/0050173 A1 | 2/2018 | Kearns | |
| 2018/0071486 A1 | 3/2018 | O'Flynn | |
| 2018/0104444 A1 | 4/2018 | Yin et al. | |
| 2018/0169377 A1 | 6/2018 | Hickmott et al. | |
| 2019/0047766 A1 | 2/2019 | Brooks et al. | |
| 2019/0083746 A1 | 3/2019 | Murray et al. | |
| 2019/0105462 A1 | 4/2019 | Schertiger | |
| 2019/0110879 A1 | 4/2019 | Camp et al. | |
| 2019/0126004 A1 | 5/2019 | O'Brien et al. | |
| 2019/0151605 A1 | 5/2019 | McMenamin et al. | |
| 2019/0151610 A1 | 5/2019 | Fletter | |
| 2019/0216985 A1* | 7/2019 | Mcburney | A61L 27/505 |
| 2019/0255280 A1 | 8/2019 | Palmer | |
| 2019/0321593 A1 | 10/2019 | Crawford | |
| 2019/0358435 A1 | 11/2019 | Andersin et al. | |
| 2019/0381272 A1 | 12/2019 | Terry | |
| 2020/0001043 A1 | 1/2020 | Heneghan et al. | |
| 2020/0016380 A1 | 1/2020 | Murray et al. | |
| 2020/0115102 A1 | 4/2020 | Hawry | |
| 2020/0155261 A1 | 5/2020 | O'Flynn et al. | |
| 2020/0155794 A1 | 5/2020 | Ziebol | |
| 2020/0155796 A1 | 5/2020 | Hannon et al. | |
| 2020/0171218 A1 | 6/2020 | Dong et al. | |
| 2020/0179647 A1 | 6/2020 | Conway et al. | |
| 2020/0188631 A1 | 6/2020 | Hannon et al. | |
| 2020/0222659 A1 | 7/2020 | Schertiger et al. | |
| 2020/0230349 A1 | 7/2020 | McMenamin et al. | |
| 2020/0238048 A1 | 7/2020 | Palmer | |
| 2020/0246594 A1 | 8/2020 | Miller | |
| 2020/0281751 A1 | 9/2020 | Schreck et al. | |
| 2020/0345977 A1 | 11/2020 | Hickmott et al. | |
| 2020/0361076 A1* | 11/2020 | Richart | B25J 1/00 |
| 2020/0383822 A1 | 12/2020 | Palmer | |
| 2020/0391005 A1 | 12/2020 | Murray et al. | |
| 2020/0398023 A1 | 12/2020 | Conway et al. | |
| 2020/0398024 A1 | 12/2020 | Fletter et al. | |
| 2021/0008361 A1 | 1/2021 | Aronson | |
| 2021/0100979 A1 | 4/2021 | Donnelly et al. | |
| 2021/0113808 A1 | 4/2021 | Yin et al. | |
| 2021/0187238 A1* | 6/2021 | O'Brien | B65D 43/22 |
| 2021/0212808 A1* | 7/2021 | Wu | A61F 2/0095 |
| 2021/0283367 A1 | 9/2021 | Peters | |
| 2021/0290894 A1* | 9/2021 | Palmer | A61M 25/0111 |
| 2021/0290895 A1 | 9/2021 | Nielsen et al. | |
| 2021/0402135 A1 | 12/2021 | McMenamin et al. | |
| 2022/0023585 A1 | 1/2022 | Schertiger et al. | |
| 2022/0054295 A1 | 2/2022 | Becker | |
| 2022/0112018 A1 | 4/2022 | Montano et al. | |
| 2022/0117850 A1 | 4/2022 | Romeo et al. | |
| 2022/0142810 A1 | 5/2022 | Whittaker | |
| 2022/0241549 A1 | 8/2022 | Murray et al. | |
| 2022/0273837 A1 | 9/2022 | Paul et al. | |
| 2022/0362536 A1 | 11/2022 | Nguyen et al. | |
| 2023/0058911 A1 | 2/2023 | Nabors et al. | |
| 2023/0072221 A1 | 3/2023 | Donnelly et al. | |
| 2023/0073264 A1 | 3/2023 | Kandrac et al. | |
| 2023/0075906 A1 | 3/2023 | Piashevich et al. | |
| 2023/0077075 A1 | 3/2023 | Kandrac et al. | |
| 2023/0166073 A1* | 6/2023 | Radmer | A61M 25/002 |
| | | | 604/544 |
| 2023/0293849 A1 | 9/2023 | Hughett, Sr. et al. | |
| 2023/0364379 A1 | 11/2023 | Hughett, Sr. et al. | |
| 2024/0108850 A1 | 4/2024 | Yin et al. | |
| 2024/0269426 A1 | 8/2024 | Siddiqui | |
| 2024/0325685 A1 | 10/2024 | Daw et al. | |
| 2025/0082897 A1 | 3/2025 | Pfleger | |
| 2025/0114231 A1 | 4/2025 | Legaspi et al. | |
| 2025/0288774 A1 | 9/2025 | Kulkarni et al. | |
| 2025/0289618 A1 | 9/2025 | Simonsen et al. | |
| 2025/0325785 A1 | 10/2025 | Kulkarni et al. | |

FOREIGN PATENT DOCUMENTS

| | | |
|---|---|---|
| AU | 2022354188 A1 | 3/2024 |
| BR | PI0803737 A2 | 1/2010 |
| CA | 763930 A | 7/1967 |
| CA | 2770300 A1 | 2/2011 |
| CA | 2769026 C | 4/2015 |
| CA | 3083014 A1 | 5/2019 |
| CN | 1106744 A | 8/1995 |
| CN | 2532840 Y | 1/2003 |
| CN | 2907580 Y | 6/2007 |
| CN | 101035573 A | 9/2007 |
| CN | 101365501 A | 2/2009 |
| CN | 102939127 A | 2/2013 |
| CN | 102939129 A | 2/2013 |
| CN | 102973986 A | 3/2013 |
| CN | 102973987 A | 3/2013 |

(56) References Cited

FOREIGN PATENT DOCUMENTS

| | | | |
|---|---|---|---|
| CN | 107088243 | A | 8/2017 |
| CN | 111870742 | A | 11/2020 |
| CN | 217015042 | U | 7/2022 |
| CN | 116056746 | A | 5/2023 |
| DE | 352014 | C | 4/1922 |
| DE | 1913976 | U | 4/1965 |
| DE | 4135502 | C1 | 2/1993 |
| DE | 4303899 | A1 | 8/1994 |
| DE | 19826746 | C1 | 11/1999 |
| DE | 10038521 | A1 | 2/2002 |
| DE | 10213411 | A1 | 10/2003 |
| DE | 10259002 | A1 | 10/2003 |
| DE | 10334372 | A1 | 2/2005 |
| DE | 202005009946 | U1 | 9/2005 |
| DE | 202005009947 | U1 | 9/2005 |
| DE | 102007018275 | A1 | 3/2008 |
| DE | 102009025347 | A1 | 12/2010 |
| DE | 202012000538 | U1 | 3/2012 |
| DE | 202011107059 | U1 | 1/2013 |
| DE | 202013002466 | U1 | 3/2013 |
| DE | 102011085864 | A1 | 5/2013 |
| DE | 102012000844 | A1 | 7/2013 |
| DE | 102016120294 | A1 | 4/2018 |
| DE | 112018000170 | T5 | 10/2019 |
| EP | 0055023 | A2 | 6/1982 |
| EP | 0182409 | A1 | 5/1986 |
| EP | 0184629 | A2 | 6/1986 |
| EP | 0187846 | A1 | 7/1986 |
| EP | 0193406 | A2 | 9/1986 |
| EP | 0218203 | A1 | 4/1987 |
| EP | 0236458 | A1 | 9/1987 |
| EP | 247559 | A1 | 12/1987 |
| EP | 0252918 | A1 | 1/1988 |
| EP | 0298634 | A1 | 1/1989 |
| EP | 0303487 | A2 | 2/1989 |
| EP | 0335564 | A1 | 10/1989 |
| EP | 0352043 | A1 | 1/1990 |
| EP | 0390720 | A1 | 10/1990 |
| EP | 0407218 | A1 | 1/1991 |
| EP | 0217771 | B1 | 12/1991 |
| EP | 0471553 | A1 | 2/1992 |
| EP | 0479935 | A1 | 4/1992 |
| EP | 0528965 | A1 | 3/1993 |
| EP | 0553960 | A1 | 8/1993 |
| EP | 0590104 | A1 | 4/1994 |
| EP | 0598191 | A1 | 5/1994 |
| EP | 0663196 | A1 | 7/1995 |
| EP | 0677299 | A1 | 10/1995 |
| EP | 0680895 | A1 | 11/1995 |
| EP | 0685179 | A1 | 12/1995 |
| EP | 0699086 | A1 | 3/1996 |
| EP | 0767639 | A1 | 4/1997 |
| EP | 0768069 | A1 | 4/1997 |
| EP | 0795339 | A1 | 9/1997 |
| EP | 0815037 | A1 | 1/1998 |
| EP | 0909249 | A1 | 4/1999 |
| EP | 0923398 | A1 | 6/1999 |
| EP | 0935478 | A1 | 8/1999 |
| EP | 0959930 | A1 | 12/1999 |
| EP | 0977610 | A2 | 2/2000 |
| EP | 1018323 | A1 | 7/2000 |
| EP | 1023882 | A1 | 8/2000 |
| EP | 1047360 | A1 | 11/2000 |
| EP | 1115450 | A1 | 7/2001 |
| EP | 1131022 | A1 | 9/2001 |
| EP | 1175355 | A1 | 1/2002 |
| EP | 1237615 | A1 | 9/2002 |
| EP | 1245205 | A2 | 10/2002 |
| EP | 1308146 | A1 | 5/2003 |
| EP | 1321163 | A1 | 6/2003 |
| EP | 1347723 | A1 | 10/2003 |
| EP | 1406690 | A2 | 4/2004 |
| EP | 1409060 | A2 | 4/2004 |
| EP | 1090656 | B1 | 5/2004 |
| EP | 1420846 | A1 | 5/2004 |
| EP | 1420847 | A2 | 5/2004 |
| EP | 1427467 | A2 | 6/2004 |
| EP | 1485158 | A2 | 12/2004 |
| EP | 1498151 | A2 | 1/2005 |
| EP | 1567219 | A1 | 8/2005 |
| EP | 1578308 | A1 | 9/2005 |
| EP | 1145729 | B1 | 11/2005 |
| EP | 1606196 | A2 | 12/2005 |
| EP | 1615690 | A1 | 1/2006 |
| EP | 1629799 | A1 | 3/2006 |
| EP | 1629860 | | 3/2006 |
| EP | 1641510 | A1 | 4/2006 |
| EP | 1642610 | | 4/2006 |
| EP | 1642611 | | 4/2006 |
| EP | 1695678 | A1 | 8/2006 |
| EP | 1357868 | B1 | 9/2006 |
| EP | 1723980 | A2 | 11/2006 |
| EP | 1744803 | A2 | 1/2007 |
| EP | 1757251 | A2 | 2/2007 |
| EP | 1788990 | A1 | 5/2007 |
| EP | 1793938 | A1 | 6/2007 |
| EP | 1799163 | A1 | 6/2007 |
| EP | 1824534 | A2 | 8/2007 |
| EP | 1824549 | A2 | 8/2007 |
| EP | 1858575 | A1 | 11/2007 |
| EP | 1904003 | A2 | 4/2008 |
| EP | 1948279 | A1 | 7/2008 |
| EP | 1955683 | A1 | 8/2008 |
| EP | 2060296 | A1 | 5/2009 |
| EP | 2106821 | A1 | 10/2009 |
| EP | 2275058 | A1 | 1/2011 |
| EP | 2292293 | A1 | 3/2011 |
| EP | 2292294 | A1 | 3/2011 |
| EP | 2308542 | A1 | 4/2011 |
| EP | 2423125 | A1 | 2/2012 |
| EP | 2423126 | A1 | 2/2012 |
| EP | 2423127 | A1 | 2/2012 |
| EP | 2450076 | A1 | 5/2012 |
| EP | 2459264 | A1 | 6/2012 |
| EP | 2464411 | A1 | 6/2012 |
| EP | 2468347 | A1 | 6/2012 |
| EP | 2500056 | A2 | 9/2012 |
| EP | 2515988 | A1 | 10/2012 |
| EP | 1786501 | B1 | 11/2012 |
| EP | 2542291 | A1 | 1/2013 |
| EP | 1578468 | B1 | 4/2013 |
| EP | 2574354 | A1 | 4/2013 |
| EP | 2424470 | B1 | 8/2013 |
| EP | 2504054 | B1 | 9/2013 |
| EP | 2644224 | A2 | 10/2013 |
| EP | 1962937 | B1 | 8/2014 |
| EP | 2774648 | A1 | 9/2014 |
| EP | 2515985 | B1 | 12/2014 |
| EP | 2686054 | B1 | 12/2014 |
| EP | 2908897 | A1 | 8/2015 |
| EP | 2898918 | A3 | 9/2015 |
| EP | 2914222 | A1 | 9/2015 |
| EP | 2967968 | A1 | 1/2016 |
| EP | 1852139 | B1 | 5/2016 |
| EP | 2777747 | B1 | 5/2017 |
| EP | 3199130 | A1 | 8/2017 |
| EP | 3231471 | A1 | 10/2017 |
| EP | 3078393 | B1 | 11/2017 |
| EP | 3272385 | A1 | 1/2018 |
| EP | 3222316 | B1 | 5/2018 |
| EP | 3352831 | A1 | 8/2018 |
| EP | 2782629 | B1 | 4/2019 |
| EP | 3313494 | B1 | 5/2019 |
| EP | 3478353 | A1 | 5/2019 |
| EP | 2826514 | B1 | 6/2019 |
| EP | 3490654 | A1 | 6/2019 |
| EP | 2946803 | B1 | 7/2019 |
| EP | 3551103 | A1 | 10/2019 |
| EP | 3566739 | A1 | 11/2019 |
| EP | 3570925 | A1 | 11/2019 |
| EP | 3092024 | B1 | 12/2019 |
| EP | 3583972 | A2 | 12/2019 |
| EP | 3388103 | B1 | 1/2020 |
| EP | 3590573 | A1 | 1/2020 |

(56) References Cited

FOREIGN PATENT DOCUMENTS

| | | | |
|---|---|---|---|
| EP | 3079752 B1 | 4/2020 |
| EP | 3100758 B1 | 4/2020 |
| EP | 2826515 B1 | 5/2020 |
| EP | 3079748 B1 | 5/2020 |
| EP | 3651844 A1 | 5/2020 |
| EP | 2651485 B1 | 6/2020 |
| EP | 3038690 B1 | 7/2020 |
| EP | 3119464 B1 | 9/2020 |
| EP | 3132823 B1 | 9/2020 |
| EP | 3299056 B1 | 9/2020 |
| EP | 3701993 A1 | 9/2020 |
| EP | 3709940 A1 | 9/2020 |
| EP | 3710095 A1 | 9/2020 |
| EP | 3711806 A1 | 9/2020 |
| EP | 3711807 A1 | 9/2020 |
| EP | 3711808 A1 | 9/2020 |
| EP | 3713632 A2 | 9/2020 |
| EP | 3392167 B1 | 10/2020 |
| EP | 2468346 B1 | 11/2020 |
| EP | 3077031 B1 | 11/2020 |
| EP | 3738640 A1 | 11/2020 |
| EP | 3769803 A2 | 1/2021 |
| EP | 2995268 B1 | 3/2021 |
| EP | 3793627 A1 | 3/2021 |
| EP | 2968833 B1 | 5/2021 |
| EP | 3952973 A1 | 2/2022 |
| EP | 3082929 B1 | 3/2022 |
| EP | 3310421 B1 | 3/2022 |
| EP | 3725355 B1 | 5/2022 |
| EP | 2688629 B1 | 12/2022 |
| ES | 2645658 B1 | 10/2018 |
| FR | 1558162 A | 2/1969 |
| FR | 96086 E | 5/1972 |
| FR | 2127704 A5 | 10/1972 |
| FR | 2351634 A1 | 12/1977 |
| FR | 2731345 A1 | 9/1996 |
| FR | 2794638 A1 | 12/2000 |
| FR | 2855399 A1 | 12/2004 |
| FR | 3042716 B1 | 10/2021 |
| GB | 322426 A | 12/1929 |
| GB | 1131865 A | 10/1968 |
| GB | 2007507 A | 5/1979 |
| GB | 2106784 A | 4/1983 |
| GB | 2150938 A | 7/1985 |
| GB | 2187670 A | 9/1987 |
| GB | 2231801 A | 11/1990 |
| GB | 2239804 A | 7/1991 |
| GB | 2319507 | 5/1998 |
| GB | 2284764 B | 8/1998 |
| GB | 2427362 B | 9/2008 |
| GB | 2462267 A | 2/2010 |
| GB | 2469824 B | 8/2011 |
| GB | 2532459 B | 12/2016 |
| GB | 2565585 A | 2/2019 |
| GB | 2561843 B | 9/2021 |
| JP | S5512265 B2 | 3/1980 |
| JP | S59218157 A | 12/1984 |
| JP | S59228856 A | 12/1984 |
| JP | H0218157 A | 1/1990 |
| JP | H09206370 A | 8/1997 |
| JP | H10151094 A | 6/1998 |
| JP | H10277144 A | 10/1998 |
| JP | 2001500414 A | 1/2001 |
| JP | 200150329 A | 2/2001 |
| JP | 2002530148 A | 9/2002 |
| JP | 2002282275 A | 10/2002 |
| JP | 2002543885 A | 12/2002 |
| JP | 2007501656 A | 2/2007 |
| JP | 2007167158 A | 7/2007 |
| JP | 2008-51549 A | 3/2008 |
| JP | 2008508077 A | 3/2008 |
| JP | 2008526377 A | 7/2008 |
| JP | 2009125583 A | 6/2009 |
| JP | 2010538106 A | 12/2010 |
| JP | 2011510110 A | 3/2011 |
| JP | 2013500125 A | 1/2013 |
| JP | 2013515572 | 5/2013 |
| KR | 1020160035437 A | 3/2016 |
| RU | 2009105497 A | 8/2010 |
| WO | 1984001102 A1 | 3/1984 |
| WO | 198401296 A1 | 4/1984 |
| WO | 1986000816 A1 | 2/1986 |
| WO | 1986006284 A1 | 11/1986 |
| WO | 1987001582 A1 | 3/1987 |
| WO | 1989003232 A1 | 4/1989 |
| WO | 1989009626 A1 | 10/1989 |
| WO | 1990004431 A1 | 5/1990 |
| WO | 1991005577 A1 | 5/1991 |
| WO | 1991010466 A1 | 7/1991 |
| WO | 1991017728 A1 | 11/1991 |
| WO | 1992008426 A1 | 5/1992 |
| WO | 1992010220 A1 | 6/1992 |
| WO | 1992011826 A1 | 7/1992 |
| WO | 1992019192 A1 | 11/1992 |
| WO | 1993000054 A1 | 1/1993 |
| WO | 9311821 A1 | 6/1993 |
| WO | 9314806 A1 | 8/1993 |
| WO | 1994006377 A1 | 3/1994 |
| WO | 1994016747 A1 | 8/1994 |
| WO | 1994026215 A1 | 11/1994 |
| WO | 1995008968 A1 | 4/1995 |
| WO | 1995009667 A1 | 4/1995 |
| WO | 1995017862 A1 | 7/1995 |
| WO | 1995034253 A1 | 12/1995 |
| WO | 1996000541 A1 | 1/1996 |
| WO | 1996004119 A1 | 2/1996 |
| WO | 9607447 A1 | 3/1996 |
| WO | 1996019254 A1 | 6/1996 |
| WO | 1996026688 A1 | 9/1996 |
| WO | 1996030277 A1 | 10/1996 |
| WO | 1996034587 A1 | 11/1996 |
| WO | 9641653 A1 | 12/1996 |
| WO | 1996038192 A1 | 12/1996 |
| WO | 1996039096 A1 | 12/1996 |
| WO | 1997025947 A1 | 7/1997 |
| WO | 1997026937 A1 | 7/1997 |
| WO | 1997041811 A1 | 11/1997 |
| WO | 1998006642 | 2/1998 |
| WO | 1998011932 | 3/1998 |
| WO | 1998019729 | 5/1998 |
| WO | 9846176 A1 | 10/1998 |
| WO | 1999007313 A1 | 2/1999 |
| WO | 1999030761 A1 | 6/1999 |
| WO | 1999036009 A1 | 7/1999 |
| WO | 2000016843 | 3/2000 |
| WO | 2000025848 A2 | 5/2000 |
| WO | 0030696 A1 | 6/2000 |
| WO | 2000030575 A1 | 6/2000 |
| WO | 2000047494 A1 | 8/2000 |
| WO | 2001043807 A1 | 6/2001 |
| WO | 0152763 A1 | 7/2001 |
| WO | 2001093935 A1 | 12/2001 |
| WO | 2002036192 A1 | 5/2002 |
| WO | 2002053070 A1 | 7/2002 |
| WO | 2002060361 A2 | 8/2002 |
| WO | 03008028 A2 | 1/2003 |
| WO | 2003002177 | 1/2003 |
| WO | 2003002178 A2 | 1/2003 |
| WO | 2003008029 | 1/2003 |
| WO | 2003022333 A1 | 3/2003 |
| WO | 2003064279 A1 | 8/2003 |
| WO | 03092779 A1 | 11/2003 |
| WO | 03093357 A1 | 11/2003 |
| WO | 2004004611 A1 | 1/2004 |
| WO | 2004004796 A1 | 1/2004 |
| WO | 2004030722 A2 | 4/2004 |
| WO | 2004032992 A2 | 4/2004 |
| WO | 2004045696 | 6/2004 |
| WO | 2004050155 A1 | 6/2004 |
| WO | 2004052440 A1 | 6/2004 |
| WO | 2004056290 A1 | 7/2004 |
| WO | 2004056414 A1 | 7/2004 |
| WO | 2004056909 A1 | 7/2004 |
| WO | 2004075944 A2 | 9/2004 |

(56)                References Cited

FOREIGN PATENT DOCUMENTS

| WO | 2004089454 | A1 | 10/2004 |
| WO | 2005004964 | A1 | 1/2005 |
| WO | 2005014055 | A2 | 2/2005 |
| WO | 2005061035 | A1 | 7/2005 |
| WO | 2005092418 | A1 | 10/2005 |
| WO | 2006005349 | A2 | 1/2006 |
| WO | 2006009509 | A1 | 1/2006 |
| WO | 2006009596 | A1 | 1/2006 |
| WO | 2006017439 | A2 | 2/2006 |
| WO | 2006021590 | A1 | 3/2006 |
| WO | 2006027349 | A1 | 3/2006 |
| WO | 2006033234 | A1 | 3/2006 |
| WO | 2006037321 | A1 | 4/2006 |
| WO | 2006097109 | A2 | 9/2006 |
| WO | 2006110695 | A2 | 10/2006 |
| WO | 2006112782 | A1 | 10/2006 |
| WO | 2006130776 | A2 | 12/2006 |
| WO | 2007001526 | A2 | 1/2007 |
| WO | 2007038988 | A1 | 4/2007 |
| WO | 2007050685 |    | 5/2007 |
| WO | 2007083033 | A2 | 7/2007 |
| WO | 2008089770 | A1 | 7/2008 |
| WO | 2008104573 | A2 | 9/2008 |
| WO | 2008104603 | A1 | 9/2008 |
| WO | 2008138351 | A1 | 11/2008 |
| WO | 2008138352 | A1 | 11/2008 |
| WO | 2008151074 | A1 | 12/2008 |
| WO | 2009000277 | A1 | 12/2008 |
| WO | 2009012336 | A1 | 1/2009 |
| WO | 2009017541 | A1 | 2/2009 |
| WO | 2009043872 | A1 | 4/2009 |
| WO | 2009068043 | A2 | 6/2009 |
| WO | 2009080265 | A1 | 7/2009 |
| WO | 2009108243 | A1 | 9/2009 |
| WO | 2010006620 | A1 | 1/2010 |
| WO | 2010041084 | A1 | 4/2010 |
| WO | 2010054659 | A1 | 5/2010 |
| WO | 2010054666 | A1 | 5/2010 |
| WO | 2010129362 | A1 | 11/2010 |
| WO | 2010130261 | A1 | 11/2010 |
| WO | 2010149174 | A1 | 12/2010 |
| WO | 2010149175 | A1 | 12/2010 |
| WO | 2010151682 | A2 | 12/2010 |
| WO | 2011011023 | A1 | 1/2011 |
| WO | 2011014201 | A1 | 2/2011 |
| WO | 2011019359 | A1 | 2/2011 |
| WO | 2011026929 | A1 | 3/2011 |
| WO | 2011026930 | A1 | 3/2011 |
| WO | 2011063816 | A1 | 6/2011 |
| WO | 2011073403 | A1 | 6/2011 |
| WO | 2011076211 | A1 | 6/2011 |
| WO | 2011079129 | A1 | 6/2011 |
| WO | 2011109393 | A1 | 9/2011 |
| WO | 2012016570 | A2 | 2/2012 |
| WO | 2012016571 | A2 | 2/2012 |
| WO | 2012079590 | A1 | 6/2012 |
| WO | 2012085124 | A1 | 6/2012 |
| WO | 2012126474 | A1 | 9/2012 |
| WO | 2012134804 | A1 | 10/2012 |
| WO | 2012139214 | A1 | 10/2012 |
| WO | 2013010745 | A1 | 1/2013 |
| WO | 2013029621 | A1 | 3/2013 |
| WO | 2013075725 | A1 | 5/2013 |
| WO | 2014062225 | A1 | 4/2014 |
| WO | 2014081859 | A1 | 5/2014 |
| WO | 2014142917 | A1 | 9/2014 |
| WO | 2014142923 | A1 | 9/2014 |
| WO | 2014165046 | A1 | 10/2014 |
| WO | 15069843   | A2 | 5/2015 |
| WO | 2015075841 | A1 | 5/2015 |
| WO | 15090338   | A1 | 6/2015 |
| WO | 2015089189 | A2 | 6/2015 |
| WO | 2015105942 | A1 | 7/2015 |
| WO | 15142506   | A1 | 9/2015 |
| WO | 2015184365 | A1 | 12/2015 |
| WO | 201603323  | A1 | 1/2016 |
| WO | 2016008493 | A1 | 1/2016 |
| WO | 2016116915 | A1 | 7/2016 |
| WO | 2016206701 | A1 | 12/2016 |
| WO | 2017185052 | A1 | 10/2017 |
| WO | 2018029279 | A1 | 2/2018 |
| WO | 2018059637 | A1 | 4/2018 |
| WO | 2018134748 | A1 | 7/2018 |
| WO | 2018150975 | A1 | 8/2018 |
| WO | 2018156589 | A2 | 8/2018 |
| WO | 2018219433 | A1 | 12/2018 |
| WO | 2019002066 | A2 | 1/2019 |
| WO | 2019014344 | A1 | 1/2019 |
| WO | 2019070984 | A1 | 4/2019 |
| WO | 2019083104 | A1 | 5/2019 |
| WO | 2019083839 | A1 | 5/2019 |
| WO | 2019099845 | A1 | 5/2019 |
| WO | 2019099975 | A2 | 5/2019 |
| WO | 2019113203 | A1 | 6/2019 |
| WO | 2019123004 | A1 | 6/2019 |
| WO | 2019245679 | A1 | 12/2019 |
| WO | 2020006527 | A1 | 1/2020 |
| WO | 2020015804 | A1 | 1/2020 |
| WO | 2020106822 | A1 | 5/2020 |
| WO | 2020125908 | A1 | 6/2020 |
| WO | 2020223146 | A1 | 11/2020 |
| WO | 2020237286 | A1 | 12/2020 |
| WO | 2020251961 | A1 | 12/2020 |
| WO | 2020252003 | A1 | 12/2020 |
| WO | 2020263859 | A1 | 12/2020 |
| WO | 2021034487 | A1 | 2/2021 |
| WO | 2021041703 | A1 | 3/2021 |
| WO | 2021051158 | A1 | 3/2021 |
| WO | 2021077103 | A1 | 4/2021 |
| WO | 2021087099 | A1 | 5/2021 |
| WO | 2021092271 | A1 | 5/2021 |
| WO | 2021097519 | A1 | 5/2021 |
| WO | 2021108115 | A1 | 6/2021 |
| WO | 2021115840 | A1 | 6/2021 |
| WO | 2021127040 | A1 | 6/2021 |
| WO | 2021183718 | A1 | 9/2021 |
| WO | 2022031520 | A1 | 2/2022 |
| WO | 2022031550 | A1 | 2/2022 |
| WO | 2022056263 | A2 | 3/2022 |
| WO | 2022223978 | A1 | 10/2022 |
| WO | 2022223980 | A1 | 10/2022 |
| WO | 2022223983 | A1 | 10/2022 |
| WO | 2022223985 | A1 | 10/2022 |
| WO | 2022223987 | A1 | 10/2022 |
| WO | 2022260831 | A1 | 12/2022 |
| WO | 2023003682 | A1 | 1/2023 |
| WO | 2023055832 | A1 | 4/2023 |
| WO | 2023180707 | A1 | 9/2023 |
| WO | 2023211421 | A1 | 11/2023 |
| WO | 2024112323 | A1 | 5/2024 |
| WO | 2024112324 | A1 | 5/2024 |
| WO | 2024112325 | A1 | 5/2024 |
| WO | 2024112799 | A1 | 5/2024 |
| WO | 2024112805 | A1 | 5/2024 |

OTHER PUBLICATIONS

"Tripartite Biocompatibility Guidance for Medical Devices," DSMA (Apr. 24, 1987).

Akzo Nobel, "Ethomeen C/25 technical data sheet" Mar. 10, 2009.

Amirkhai IL et al., "Nitric Oxide Complexes of Trimethylaluminium" Journal of Organometallic Chemistry, 149 (1978).

Angus "Chemie GmbHTechnical Data Sheet", AMP-95, TDS 10A (2000).

AU 2014248744 filed Jul. 9, 2015 Examiner's Report dated Jul. 26, 2017.

AU 2015306630 filed Feb. 2, 2017 Office Action dated Aug. 2, 2018.

BR PI 0506836-3 filed Jan. 18, 2005, Technical Report dated Jul. 28, 2015.

BR1120170040301 filed Feb. 21, 2017 Office Action dated Aug. 20, 2019.

(56) References Cited

OTHER PUBLICATIONS

CA 2,769,026 filed Jan. 24, 2012 First Examination Report dated Nov. 4, 2013.
CN 201080058895.4 filed Jun. 21, 2012 First Office Action dated Feb. 27, 2014.
CN 201080058895.4 filed Jun. 21, 2012 Second Office Action dated Nov. 3, 2014.
CN 201080058895.4 filed Jun. 21, 2012 Third Office Action dated May 4, 2015.
CN 201480013064.3 filed Sep. 8, 2015 Office Action dated Jun. 29, 2017.
CN 201480013064.3 filed Sep. 8, 2015 Office Action dated Oct. 10, 2016.
CN 20158004662.3 filed Feb. 24, 2017 Office Action dated Jul. 8, 2019.
CN 20158004662.3 filed Feb. 24, 2017 Office Action dated Sep. 20, 2019.
EP 09848341.5 filed Feb. 27, 2012 extended European Search Report dated Apr. 4, 2013.
EP 09848341.5 filed Feb. 27, 2012 supplemental European Search Report dated Nov. 8, 2013.
EP 10840071.4 filed Jul. 4, 2012 Exam Report dated Apr. 29, 2014.
EP 10840071.4 filed Jul. 4, 2012 extended European Search Report dated Apr. 17, 2013.
EP 10840071.4 filed Jul. 4, 2012 Notice of Opposition dated Apr. 24, 2017.
EP 10840071.4 filed Jul. 4, 2012 Office Action dated Jul. 9, 2015.
EP 11751198.0 filed Sep. 28, 2012 Exam Report dated Feb. 7, 2014.
EP 11751198.0 filed Sep. 28, 2012 extended European search report dated Jul. 9, 2013.
EP 14779919.1 filed Sep. 10, 2015 Extended European Search Report dated Aug. 23, 2016.
EP 14779919.1 filed Sep. 10, 2015 Office Action dated Jul. 4, 2017.
EP 15836062.8 filed Feb. 17, 2017 Extended European Search Report dated Feb. 20, 2018.
EP 15836062.8 filed Feb. 17, 2017 Office Action dated Feb. 19, 2019.
EP 16171279.9 filed May 25, 2016 Extended European Search Report, dated Aug. 23, 2016.
EP 16171279.9 filed May 25, 2016 Intent to Grant, dated Jun. 13, 2017.
EP 17201044.9 filed Nov. 10, 2017 Extended European Search Report dated Jan. 18, 2018.
EP 17201044.9 filed Nov. 10, 2017 Office Action dated Jul. 4, 2019.
Hollister, "Vapro intermittent catheter brochure" (2009).
Johnson et al. "Activities of a Nitrofurazone-Containing Urinary Catheter and a Silver Hydrogel Catheter against Multidrug-Resistant Bacteria Characteristic of Catheter-Associated Urinary Tract Infection" Antimicrobial Agents and Chemotherapy, Dec. 1999.
JP 2012-546157 filed Jun. 12, 2012 Decision of Rejection dated Aug. 21, 2015.
JP 2012-546157 filed Jun. 12, 2012 First Office Action dated Sep. 16, 2014.
JP 2015-243156 filed Dec. 14, 2015 Office Action dated Sep. 16, 2016.
JP 2016-501444 filed Sep. 11, 2015 Office Action dated Dec. 14, 2017.
JP 2017-511223 filed Feb. 24, 2017 Office Action dated Jun. 4, 2019.
Lubrizol, "Neutralizing Carbopol®* and Pemulen™* Polymers in Aqueous and Hydroalcoholic Systems" Technical Data Sheet TDS-237 Edition: Sep. 16, 2009.
Moore et al., "The Swelling of Cotton in Water: A Microscopical Study," Textile Research Journal, vol. 20, Issue 9 pp. 620-630, Sep. 1, 1950.
MX/a/2015/009904 filed Jul. 30, 2015 Office Action dated Jun. 29, 2018.
MX/a/2017/002457 filed Feb. 23, 2017 Office Action dated Sep. 4, 2019.

Newman "Intermittent Catheterization and Current Best Practices: Catheter Design and Types"; http://www.medscape.com/viewarticle/745908_8, last accessed May 31, 2013.
Newman et al. "Review of Intermittent Catheterization and Current Best Practices," Urological Nursing, vol. 31, No. 1 pp. 12-29, 48, Jan. 2011.
Norton, J.A. et al., Surgery: Basic Science and Clinical Evidence Springer, 2nd ed., 2008, p. 281.
PCT/US2006/041633 filed Oct. 25, 2006 International Preliminary Report on Patentability dated Mar. 24, 2009.
PCT/US2006/041633 filed Oct. 25, 2006 Search Report dated Aug. 12, 2008.
PCT/US2006/041633 filed Oct. 25, 2006 Written Opinion dated Aug. 12, 2008.
U.S. Appl. No. 13/662,278, filed Oct. 26, 2012 Examiner's Answer dated Jun. 2, 2017.
U.S. Appl. No. 13/662,278, filed Oct. 26, 2012 Final Office Action dated Feb. 20, 2015.
U.S. Appl. No. 13/662,278, filed Oct. 26, 2012 Final Office Action dated Oct. 19, 2016.
U.S. Appl. No. 13/662,278, filed Oct. 26, 2012 Non-Final Office Action dated Jul. 7, 2016.
U.S. Appl. No. 13/662,278, filed Oct. 26, 2012 Non-Final Office Action dated Sep. 12, 2014.
U.S. Appl. No. 13/662,278, filed Oct. 26, 2012 Non-Final Office Action dated Sep. 17, 2015.
U.S. Appl. No. 13/802,095, filed Mar. 13, 2013 Non-Final Office Action dated Aug. 15, 2014.
U.S. Appl. No. 13/802,095, filed Mar. 13, 2013 Notice of Allowance dated Nov. 28, 2014.
U.S. Appl. No. 14/681,023, filed Apr. 7, 2015 Non-Final Office Action dated Nov. 9, 2016.
U.S. Appl. No. 14/681,023, filed Apr. 7, 2015 Notice of Allowance dated Mar. 8, 2017.
U.S. Appl. No. 14/707,954, filed May 8, 2015 Non-Final Office Action dated Dec. 1, 2016.
U.S. Appl. No. 15/506,723, filed Feb. 24, 2017 Final Office Action dated Dec. 9, 2019.
U.S. Appl. No. 15/506,723, filed Feb. 24, 2017 Non-Final Office Action dated Aug. 27, 2019.
U.S. Appl. No. 15/506,723, filed Feb. 24, 2017 Notice of Allowance dated Jul. 29, 2020.
U.S. Appl. No. 15/639,844, filed Jun. 30, 2017 Non-Final Office Action dated Jul. 10, 2019.
U.S. Appl. No. 15/639,844, filed Jun. 30, 2017 Notice of Allowance dated Aug. 13, 2019.
U.S. Appl. No. 15/669,697, filed Aug. 4, 2017 Non-Final Office Action dated Oct. 18, 2018.
U.S. Appl. No. 15/669,697, filed Aug. 4, 2017 Notice of Allowance dated Mar. 1, 2019.
U.S. Appl. No. 15/724,879, filed Oct. 4, 2017 Advisory Action dated Jan. 29, 2019.
U.S. Appl. No. 15/724,879, filed Oct. 4, 2017 Examiner's Answer dated Jul. 25, 2019.
U.S. Appl. No. 15/724,879, filed Oct. 4, 2017 Final Office Action dated Dec. 4, 2018.
U.S. Appl. No. 15/724,879, filed Oct. 4, 2017 Non-Final Office Action dated Jul. 19, 2018.
U.S. Appl. No. 15/724,879, filed Oct. 4, 2017 Notice of Allowance dated Aug. 14, 2020.
U.S. Appl. No. 15/724,879, filed Oct. 4, 2017 PTAB Decision on Appeal dated Jul. 1, 2020.
U.S. Appl. No. 15/724,879, filed Oct. 4, 2017 Restriction Requirement dated Mar. 7, 2018.
U.S. Appl. No. 16/453,809, filed Jun. 26, 2019 Notice of Allowance dated Apr. 14, 2020.
U.S. Appl. No. 17/114,275, filed Dec. 7, 2020 Final Office Action dated May 23, 2023.
U.S. Appl. No. 17/114,275, filed Dec. 7, 2020 Non-Final Office Action dated Jan. 31, 2023.
U.S. Appl. No. 17/114,275, filed Dec. 7, 2020 Notice of Allowance dated Aug. 9, 2023.

(56) References Cited

OTHER PUBLICATIONS

Wong, "Hydrogels, water-absorbing polymers" Catalyst, vol. 18, Issue 1, pp. 18-21, Sep. 2007.

EP 24164460.8 filed Mar. 19, 2024 Extended European Search Report dated Jun. 19, 2024.

PCT/US2022/045084 filed Sep. 28, 2022 International Search Report and Written Opinion dated Jan. 3, 2023.

PCT/US2023/080761 filed Nov. 21, 2023 International Search Report and Written Opinion dated Apr. 9, 2024.

PCT/US2023/080769 filed Nov. 21, 2023 International Search Report and Written Opinion dated Mar. 15, 2024.

PCT/US2025/019799 filed Mar. 13, 2025 International Search Report and Written Opinion dated Jun. 4, 2025.

U.S. Appl. No. 18/019,647, filed Feb. 3, 2023 Restriction Requirement dated May 8, 2025.

U.S. Appl. No. 18/025,875, filed Mar. 10, 2023 Restriction Requirement dated Jun. 4, 2025.

PCT/US2022/026177 filed Apr. 25, 2022 International Search Report & Written Opinion dated Mar. 20, 2023.

U.S. Appl. No. 17/796,611, filed Jul. 29, 2022 Non-Final Office Action dated Mar. 20, 2025.

PCT/US2021/043771 filed Jul. 29, 2021 International Search Report and Written Opinion dated Jan. 24, 2022.

PCT/US2021/044021 filed Jul. 30, 2021 International Search Report and Written Opinion dated Jan. 24, 2022.

PCT/US2021/049867 filed Sep. 10, 2021 International Search Report and Written Opinion dated Mar. 11, 2022.

PCT/US2009/055389 filed Aug. 28, 2009 International Search Report dated Oct. 20, 2009.

PCT/US2009/055389 filed Aug. 28, 2009 Written Opinion dated Oct. 20, 2009.

PCT/US2009/055395 filed Aug. 28, 2009 International Preliminary Report on Patentability dated Jan. 31, 2012.

PCT/US2009/055395 filed Aug. 28, 2009 International Search Report dated Oct. 15, 2009.

PCT/US2009/055395 filed Aug. 28, 2009 Written Opinion dated Oct. 15, 2009.

PCT/US2010/061597 filed Dec. 21, 2010 International Preliminary Report on Patentability dated Jun. 26, 2012 and Written Opinion dated Feb. 28, 2011.

PCT/US2010/061597 filed Dec. 21, 2010 International Search Report dated Feb. 28, 2011.

PCT/US2011/026681 filed Mar. 1, 2011 International Preliminary Report on Patentability dated Sep. 4, 2012.

PCT/US2011/026681 filed Mar. 1, 2011 International Search Report dated Apr. 27, 2011.

PCT/US2011/026681 filed Mar. 1, 2011 Written Opinion dated Apr. 27, 2011.

PCT/US2014/024231 filed Mar. 12, 2014 International Search Report and Written Opinion dated Jul. 10, 2014.

PCT/US2022/029431 filed May 16, 2022 International Search Report and Written Opinion dated Sep. 15, 2022.

PCT/US2022/035565 filed Jun. 29, 2022 International Search Report and Written Opinion dated Sep. 27, 2022.

PCTUS2018054378 filed Oct. 4, 2018 International Preliminary Report on Patentability dated Jan. 2, 2019.

PCTUS2018054378 filed Oct. 4, 2018 International Search Report and Written opinion dated Jan. 2, 2019.

Peppas, "Hydrogels," Biomaterial Science: An Introduction to Materials in Medicine. 2nd Edition, pp. 100-107, Aug. 18, 2004.

Piyush Gupta et al. Hydrogels: from controlled release to pH-responsive drug delivery, May 2002, DDT vol. 7, No. 10, pp. 569-579. (Year: 2002).

RU 2015140616 filed Sep. 24, 2015 Office Action dated Feb. 21, 2018.

U.S. Appl. No. 12/091,916, filed Feb. 2, 2009 Final Office Action dated Sep. 22, 2011.

U.S. Appl. No. 12/091,916, filed Feb. 2, 2009 Non-Final Office Action dated May 10, 2011.

U.S. Appl. No. 12/091,916, filed Feb. 2, 2009 Non-Final Office Action dated Nov. 24, 2010.

U.S. Appl. No. 12/091,916, filed Feb. 2, 2009 Notice of Allowance dated Aug. 17, 2012.

U.S. Appl. No. 13/387,447, filed Mar. 22, 2012 Advisory Action dated Feb. 27, 2014.

U.S. Appl. No. 13/387,447, filed Mar. 22, 2012 Examiner's Answer dated Oct. 5, 2016.

U.S. Appl. No. 13/387,447, filed Mar. 22, 2012 Final Office Action dated Dec. 11, 2013.

U.S. Appl. No. 13/387,447, filed Mar. 22, 2012 Final Office Action dated Oct. 31, 2014.

U.S. Appl. No. 13/387,447, filed Mar. 22, 2012 Final Office Action dated Oct. 5, 2015.

U.S. Appl. No. 13/387,447, filed Mar. 22, 2012 Non-Final Office Action dated Jan. 15, 2013.

U.S. Appl. No. 13/387,447, filed Mar. 22, 2012 Non-Final Office Action dated Jul. 15, 2014.

U.S. Appl. No. 13/387,447, filed Mar. 22, 2012 Non-Final Office Action dated Jun. 6, 2013.

U.S. Appl. No. 13/387,447, filed Mar. 22, 2012 Non-Final Office Action dated Mar. 12, 2015.

U.S. Appl. No. 13/387,447, filed Mar. 22, 2012 Notice of Allowance dated Jul. 30, 2018.

U.S. Appl. No. 13/387,447, filed Mar. 22, 2012 Patent Board Decision dated Jun. 1, 2018.

U.S. Appl. No. 13/389,753, filed Mar. 20, 2012 Decision on Appeal dated Jun. 29, 2017.

U.S. Appl. No. 13/389,753, filed Mar. 20, 2012 Examiner's Answer dated Aug. 27, 2015.

U.S. Appl. No. 13/389,753, filed Mar. 20, 2012 Final Office Action dated Dec. 10, 2014.

U.S. Appl. No. 13/389,753, filed Mar. 20, 2012 Non-Final Office Action dated Jul. 21, 2014.

U.S. Appl. No. 13/389,753, filed Mar. 20, 2012 Notice of Allowance dated Jul. 5, 2017.

U.S. Appl. No. 13/516,660, filed Aug. 27, 2012 Advisory Action dated Nov. 19, 2019.

U.S. Appl. No. 13/516,660, filed Aug. 27, 2012 Advisory Action dated Sep. 22, 2016.

U.S. Appl. No. 13/516,660, filed Aug. 27, 2012 Board Decision dated Jan. 22, 2019.

U.S. Appl. No. 13/516,660, filed Aug. 27, 2012 Examiner's Answer dated Nov. 22, 2017.

U.S. Appl. No. 13/516,660, filed Aug. 27, 2012 Final Office Action dated Jun. 29, 2016.

U.S. Appl. No. 13/516,660, filed Aug. 27, 2012 Final Office Action dated Sep. 9, 2019.

U.S. Appl. No. 13/516,660, filed Aug. 27, 2012 Non-Final Office Action dated Jan. 8, 2020.

U.S. Appl. No. 13/516,660, filed Aug. 27, 2012 Non-Final Office Action dated Mar. 15, 2019.

U.S. Appl. No. 13/516,660, filed Aug. 27, 2012 Non-Final Office Action dated Mar. 8, 2016.

U.S. Appl. No. 13/516,660, filed Aug. 27, 2012 Notice of Allowance dated Oct. 27, 2020.

U.S. Appl. No. 13/582,698, filed Sep. 4, 2012 Non-Final Office Action dated Sep. 24, 2014.

U.S. Appl. No. 13/662,278, filed Oct. 26, 2012 Board Decision dated Aug. 23, 2018.

PCT/US2022/050645 filed Nov. 21, 2022 International Search Report and Written Opinion dated Jun. 28, 2023.

PCT/US2022/050646 filed Nov. 21, 2022 International Search Report and Written Opinion dated May 30, 2023.

PCT/US2022/050648 filed Nov. 21, 2022 International Search Report and Written Opinion dated Jun. 16, 2023.

PCT/US2025/023972 filed Apr. 9, 2025 International Search Report and Written Opinion dated Sep. 18, 2025.

U.S. Appl. No. 17/796,611, filed Jul. 29, 2022 Final Office Action dated Sep. 24, 2025.

U.S. Appl. No. 18/019,647, filed Feb. 3, 2023 Non-Final Office Action dated Jul. 31, 2025.

(56) References Cited

OTHER PUBLICATIONS

U.S. Appl. No. 18/025,875, filed Mar. 10, 2023 Non-Final Office Action dated Aug. 28, 2025.
U.S. Appl. No. 18/604,394, filed Mar. 13, 2024 Non-Final Office Action dated Jul. 15, 2025.
U.S. Appl. No. 18/641,181, filed Apr. 19, 2024 Restriction Requirement dated Oct. 21, 2025.
U.S. Appl. No. 17/796,611, filed Jul. 29, 2022 Advisory Action dated Nov. 28, 2025.
U.S. Appl. No. 17/796,611, filed Jul. 29, 2022 Non-Final Office Action dated Jan. 8, 2026.
U.S. Appl. No. 18/019,647, filed Feb. 3, 2023 Non-Final Office Action dated Nov. 17, 2025.
U.S. Appl. No. 18/025,875, filed Mar. 10, 2023 Notice of Allowance dated Jan. 14, 2026.
U.S. Appl. No. 18/536,063, filed Dec. 11, 2023 Non-Final Office Action dated Nov. 12, 2025.
U.S. Appl. No. 18/641,181, filed Apr. 19, 2024 Non-Final Office Action dated Jan. 12, 2026.

* cited by examiner surface S

INTERMITTENT-CATHETER ASSEMBLY AND METHODS THEREOF

PRIORITY

This application is a U.S. national stage of International Application No. PCT/US2021/043771, filed Jul. 29, 2021, which claims the benefit of priority to U.S. Provisional Patent Application No. 63/060,615, filed Aug. 3, 2020, and to U.S. Provisional Patent Application No. 63/211,922, filed Jun. 17, 2021, each of which is incorporated in its entirety into this application.

BACKGROUND

Users of urinary catheters such as intermittent catheters self-catheterize four to six times a day. As such, a simple-to-use intermittent catheter that ensures sterility before use and facilitate cleanliness after use is needed.

Disclosed herein are intermittent-catheter assemblies and methods thereof that address the foregoing.

SUMMARY

Disclosed herein is an intermittent-catheter assembly including, in some embodiments, a collapsible catheter housing and an intermittent catheter. The collapsible catheter housing includes an inner sleeve and an outer sleeve slidably mounted over the inner sleeve. The intermittent catheter includes a funnel and a catheter tube coupled to the funnel. The funnel has a funnel opening for voiding urine. The intermittent-catheter assembly has a storage state and an opened state. In the storage state, the intermittent catheter is sealed within the catheter housing. In the opened state, the catheter housing is collapsed exposing the funnel of the intermittent catheter for removal of the intermittent catheter from the catheter housing.

In some embodiments, the catheter housing further includes a cap coupled to the inner sleeve. The cap includes a pair of extension arms extending from the cap. The pair of extension arms includes a corresponding pair of inwardly protruding posts about end portions of the extension arms. The pair of posts are disposed in a pair of outwardly opening sockets in the inner sleeve.

In some embodiments, the cap is configured to pivot to one side or another side of the intermittent-catheter assembly for removal of the intermittent catheter from the catheter housing.

In some embodiments, the intermittent catheter further includes a cap coupled to the funnel by a living hinge.

In some embodiments, the funnel opening opens in a proximal end of the funnel opposite the catheter tube.

In some embodiments, the intermittent catheter further includes a cap integrated into an end portion of the funnel opposite the catheter tube.

In some embodiments, the funnel opening opens in a side of the funnel.

In some embodiments, the cap includes an annular seal around a perimeter of the cap.

In some embodiments, the seal is an 'O'-ring disposed in an annular groove around the perimeter of the cap.

In some embodiments, the intermittent-catheter assembly further includes a lubricant disposed in the inner sleeve between the inner sleeve and the catheter tube in the storage state of the intermittent-catheter assembly.

In some embodiments, the catheter housing is configured to collapse when a distal end of the inner sleeve is held against a surface and the outer sleeve is moved toward the surface. When collapsed, the catheter housing exposes the funnel of the intermittent catheter for removal of the intermittent catheter from the catheter housing.

In some embodiments, the funnel includes a plurality of ridges integrated into an outer surface of the funnel. The ridges are configured for gripping the funnel as a handle while removing the intermittent catheter from the catheter housing or voiding urine.

In some embodiments, the catheter tube includes a plurality of eyelets proximate a catheter tip. The eyelets are in fluid communication with the funnel opening.

Also disclosed herein is an intermittent-catheter assembly including, in some embodiments, a collapsible catheter housing and an intermittent catheter. The catheter housing includes an outer sleeve and a collapsible outer cover coupled to the outer sleeve. The intermittent catheter includes a funnel, a cap configured to cap a proximal opening of the funnel, and a catheter tube coupled to the funnel. The intermittent catheter is disposed in the catheter housing in a storage state of the intermittent-catheter assembly.

In some embodiments, an entirety of the funnel is disposed in the outer sleeve and a majority of the catheter tube is disposed in the outer cover in the storage state of the intermittent-catheter assembly.

In some embodiments, the intermittent-catheter assembly further includes a lubricant disposed in the outer sleeve between the outer sleeve and the catheter tube in the storage state of the intermittent-catheter assembly.

In some embodiments, the outer cover is configured to collapse when a distal end of the intermittent-catheter assembly is held against a surface and the outer sleeve is moved toward the surface. Upon collapse of the outer cover, the funnel of the intermittent catheter becomes exposed for removal of the intermittent catheter from the catheter housing.

In some embodiments, the funnel includes a plurality of ridges integrated into an outer surface of the funnel. The ridges are configured for gripping the funnel as a handle while removing the intermittent catheter from the catheter housing or voiding urine.

In some embodiments, the cap is coupled to the funnel by a living hinge.

In some embodiments, the cap is configured to cap the funnel when not actively voiding urine.

In some embodiments, the catheter tube includes a plurality of eyelets proximate a catheter tip. The eyelets are in fluid communication with the proximal opening of the funnel.

In some embodiments, an inner surface of the outer sleeve includes a plurality of seals configured to secure the intermittent catheter in the catheter housing in the storage state of the intermittent-catheter assembly. By securing the intermittent catheter in the catheter housing, the seals also maintain sterility of the intermittent catheter prior to use of the intermittent catheter.

In some embodiments, the seals are configured to prevent urine leakage from the intermittent-catheter assembly in the storage state of the intermittent-catheter assembly after use of the intermittent catheter.

In some embodiments, the seals are 'O'-rings.

Also disclosed herein is a method of an intermittent-catheter assembly. The method includes, in some embodiments, an assembly-obtaining step, an assembly-transitioning step, and a first catheter-removing step. The assembly-obtaining step includes obtaining the intermittent-catheter assembly in a storage state thereof. The intermittent-catheter assembly includes an intermittent catheter disposed in a catheter housing. The assembly-transitioning step includes transitioning the intermittent-catheter assembly into an opened state thereof. The assembly-transitioning step includes, in turn, a sleeve-grasping step, an assembly-holding step, and a sleeve-moving step. The sleeve-grasping step includes grasping an outer sleeve of the catheter housing. The assembly-holding step includes holding a distal end of the intermittent-catheter assembly against a surface by the outer sleeve. The sleeve-moving step includes moving the outer sleeve toward the surface to expose a funnel of the intermittent catheter. The first catheter-removing step includes removing the intermittent catheter from the catheter housing by a funnel of the intermittent catheter.

In some embodiments, the sleeve-moving step slides the outer sleeve over an inner sleeve of the catheter housing. The outer sleeve is mounted over the inner sleeve.

In some embodiments, the method further includes an uncapping step. The uncapping step includes uncapping a cap capping a funnel opening in a proximal end of the funnel. The cap is coupled to the funnel by a living hinge.

In some embodiments, the sleeve-moving step includes exposing a funnel opening in a side of the funnel.

In some embodiments, the method further includes an alternative uncapping step. The alternative uncapping step includes uncapping a cap capping a funnel opening in a proximal end of the funnel by pivoting the cap to one side or another side of the intermittent-catheter assembly. The cap is coupled to the inner sleeve by a pair of extension arms extending from the cap.

In some embodiments, the sleeve-moving step collapses a collapsible outer cover of the catheter housing. The outer sleeve is coupled to the outer cover.

In some embodiments, the method further includes another alternative uncapping step. The other alternative uncapping step includes uncapping a cap capping a funnel opening in a proximal end of the funnel. The cap is coupled to the funnel by a living hinge.

In some embodiments, the method further includes a first catheter-inserting step and a urine-voiding step. The first catheter-inserting step includes inserting a catheter tube of the intermittent catheter into a urethra. The urine-voiding step includes voiding urine from a bladder.

In some embodiments, the method further includes a second catheter-removing step and a second catheter-inserting step. The second catheter-removing step includes removing the catheter tube from the urethra after the urine-voiding step. The second catheter-inserting step includes inserting the intermittent catheter into the catheter housing. Optionally, the second catheter-inserting step is performed concomitantly with a capping step of capping the proximal opening of the funnel. The second catheter-inserting step with the optional capping step seals the intermittent catheter in the catheter housing and prevents residual urine leakage from the intermittent-catheter assembly in the storage state of the intermittent-catheter assembly.

These and other features of the concepts provided herein will become more apparent to those of skill in the art in view of the accompanying drawings and following description, which describe particular embodiments of such concepts in greater detail.

DRAWINGS

DESCRIPTION

Figures 1, 2, 3:
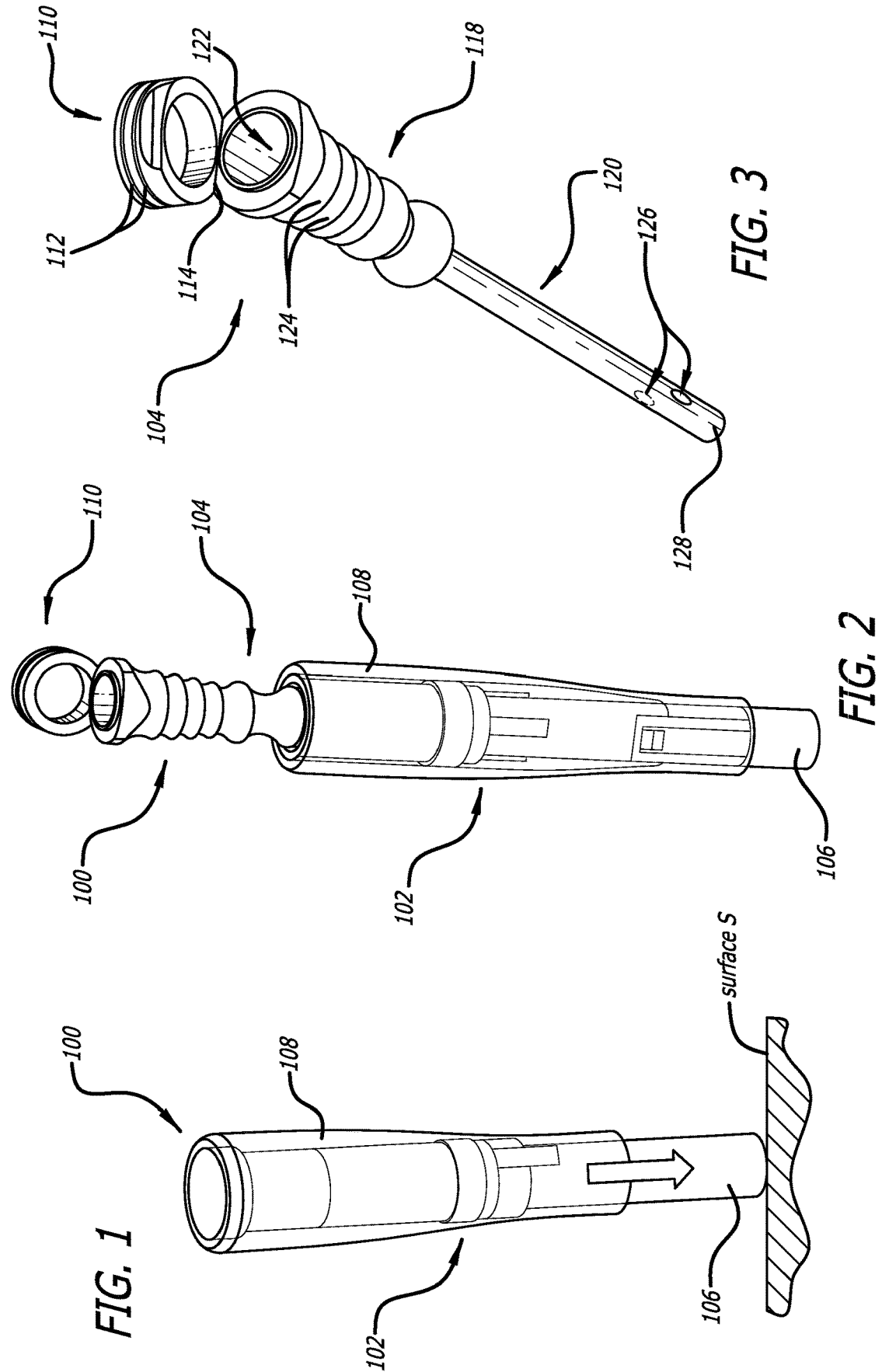
FIG. 1 illustrates a first intermittent-catheter assembly in a storage state in accordance with some embodiments.
FIG. 2 illustrates the intermittent-catheter assembly of FIG. 1 in an opened state in accordance with some embodiments.
FIG. 3 illustrates an intermittent catheter of the intermittent-catheter assembly of FIG. 1 in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

As set forth above, users of urinary catheters such as intermittent catheters self-catheterize four to six times a day. As such, a simple-to-use intermittent catheter that ensures sterility before use and facilitate cleanliness after use is needed.

Disclosed herein are intermittent-catheter assemblies and methods thereof that address the foregoing.

Intermittent-Catheter Assemblies

Figures 4, 5, 6:
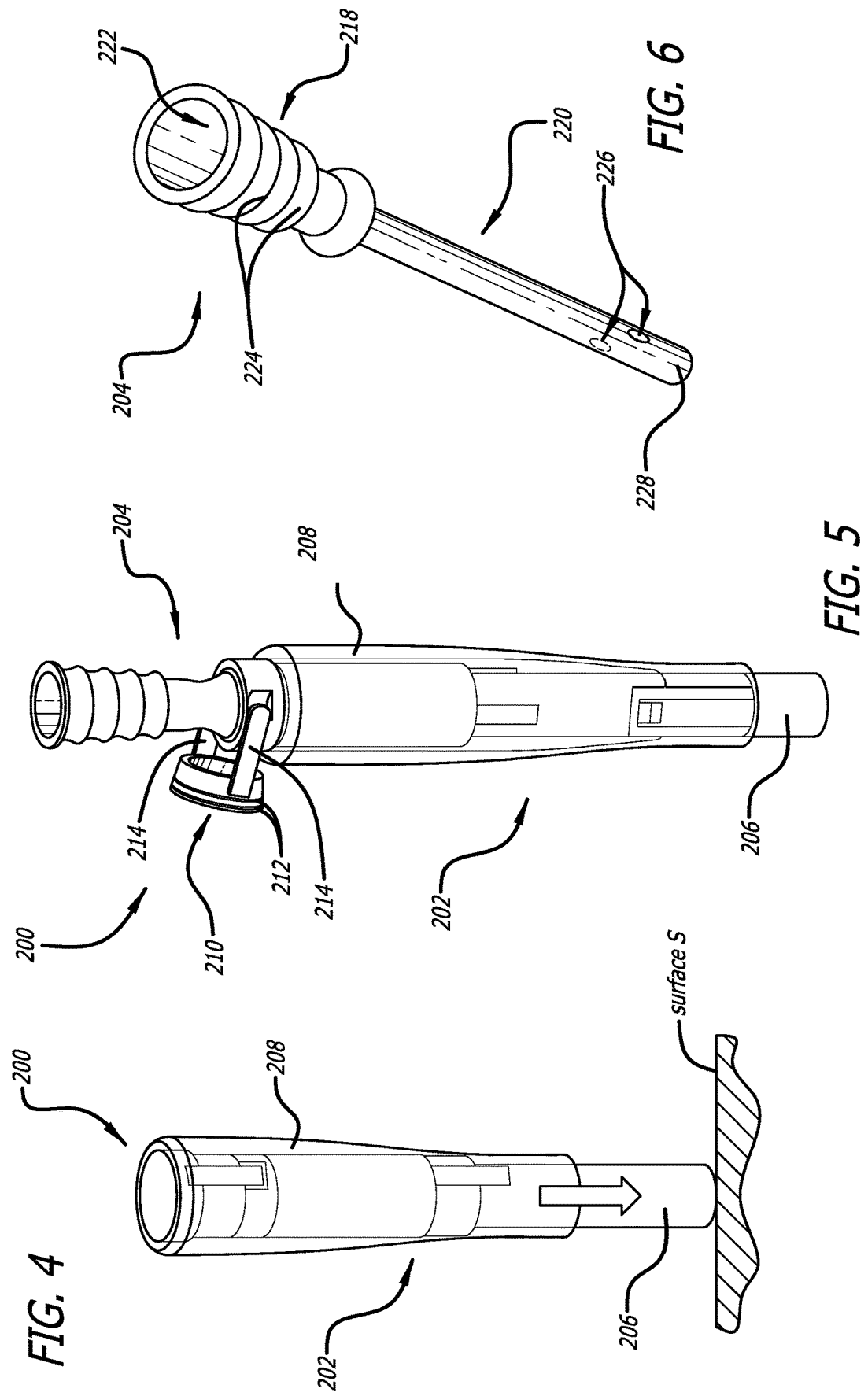
FIG. 4 illustrates a second intermittent-catheter assembly in a storage state in accordance with some embodiments.
FIG. 5 illustrates the intermittent-catheter assembly of FIG. 4 in an opened state in accordance with some embodiments.
FIG. 6 illustrates an intermittent catheter of the intermittent-catheter assembly of FIG. 4 in accordance with some embodiments.
Figures 7, 8, 9:
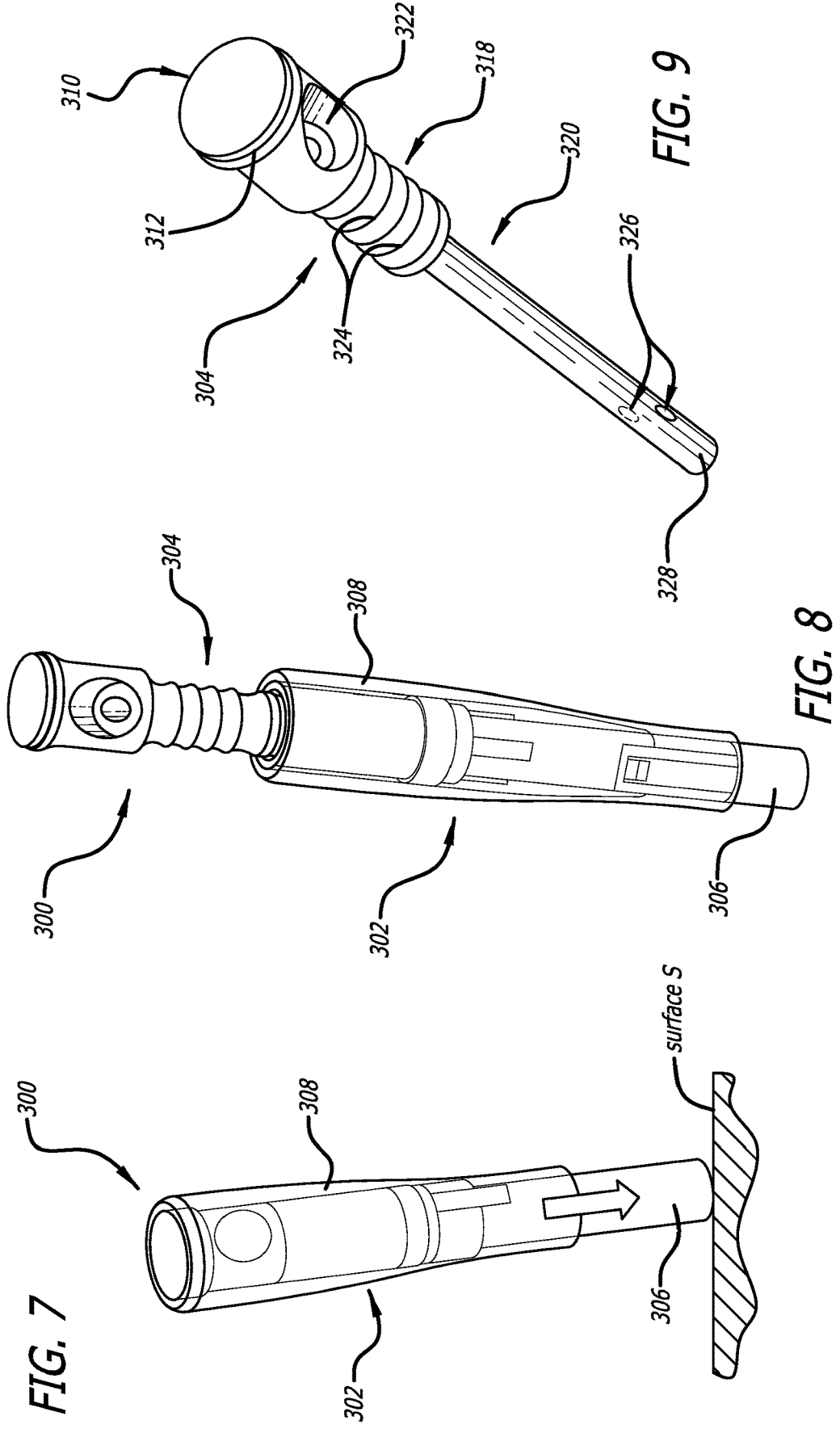
FIG. 7 illustrates a third intermittent-catheter assembly in a storage state in accordance with some embodiments.
FIG. 8 illustrates the intermittent-catheter assembly of FIG. 7 in an opened state in accordance with some embodiments.
FIG. 9 illustrates an intermittent catheter of the intermittent-catheter assembly of FIG. 7 in accordance with some embodiments.
Figures 10, 11:
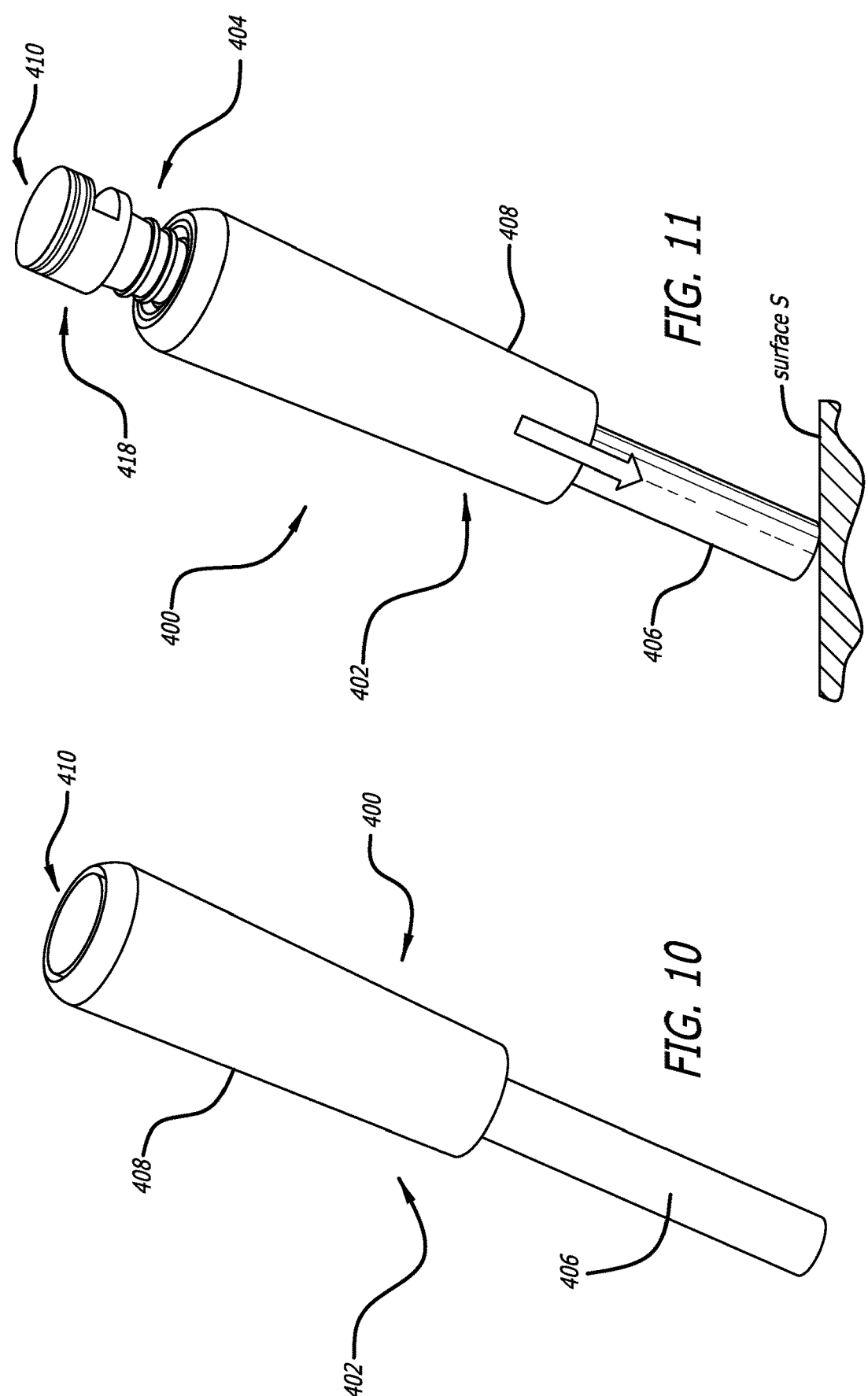
FIG. 10 illustrates a fourth intermittent-catheter assembly in a storage state in accordance with some embodiments.
FIG. 11 illustrates the intermittent-catheter assembly of FIG. 10 in an opened state in accordance with some embodiments.

FIGS. 1 and 2 illustrate a first intermittent-catheter assembly 100, FIGS. 4 and 5 illustrate a second intermittent-catheter assembly 200, FIGS. 7 and 8 illustrate a third intermittent-catheter assembly 300, and FIGS. 10-12, 15, and 16 illustrate a fourth intermittent-catheter assembly 400. Each intermittent-catheter assembly of the intermittent-catheter assemblies 100, 200, 300, and 400 is described, in turn, below.

As shown, the intermittent-catheter assembly 100, 200, 300, or 400 includes a collapsible catheter housing 102, 202, 302, or 402 and an intermittent catheter 104, 204, 304, or 404 having a storage state, an opened, and a disassembled state.

Figure 15:
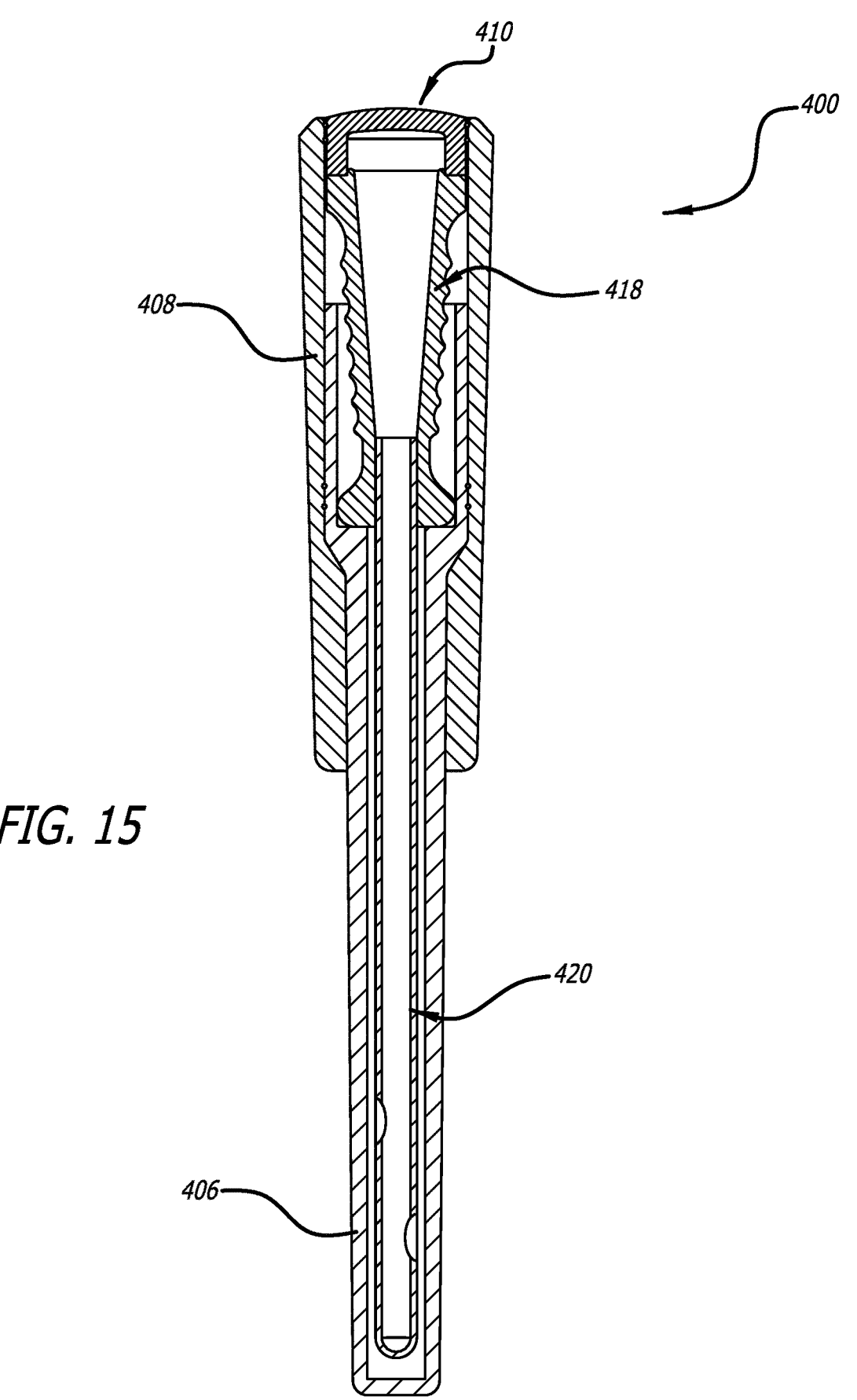
FIG. 15 illustrates a longitudinal cross-section of the intermittent-catheter assembly of FIG. 10 in the storage state in accordance with some embodiments.
Figure 16:
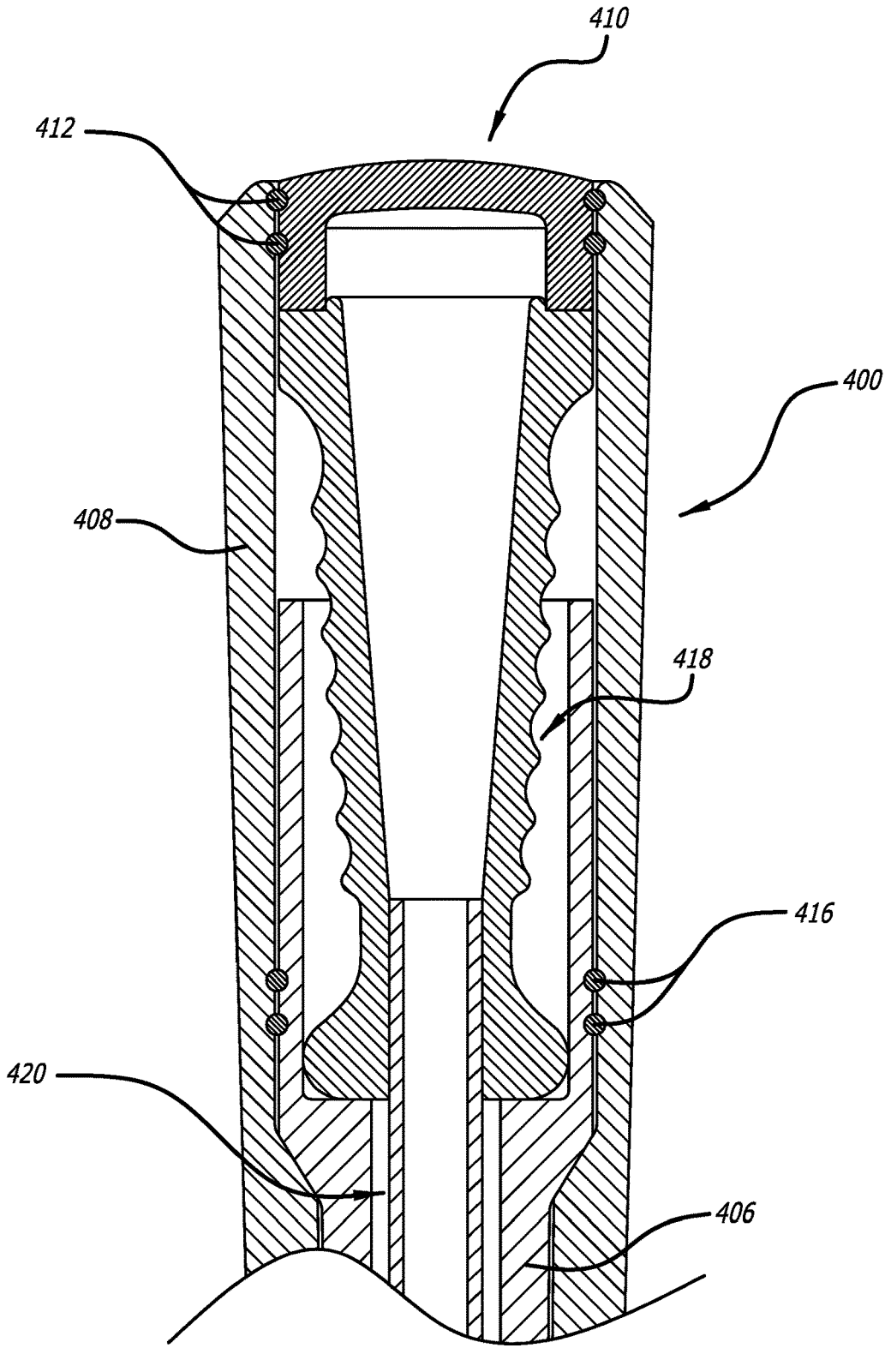
FIG. 16 illustrates a longitudinal cross-section of a proximal portion of the intermittent-catheter assembly of FIG. 10 in the storage state in accordance with some embodiments.

FIGS. 1, 4, 7, and 10 respectively show the intermittent-catheter assemblies 100, 200, 300, and 400 in their storage states, respectively. In the storage state of the intermittent-catheter assembly 100, 200, 300, or 400, the intermittent catheter 104, 204, 304, or 404 is fully disposed in the catheter housing 102, 202, 302, or 402 and sealed therein. For example, as shown in FIG. 15, an entirety of the funnel 418 of the intermittent catheter 404 is disposed in the outer sleeve 408 of the catheter housing 402 and a majority of the catheter tube 420 is disposed in the outer cover 406 of the catheter housing 402 in the storage state of the intermittent-catheter assembly 400. Sealing the intermittent catheter 104, 204, 304, or 404 in the catheter housing 102, 202, 302, or 402 is advantageous for maintaining sterility of the intermittent catheter 104, 204, 304, or 404 prior to use. Sealing the intermittent catheter 104, 204, 304, or 404 in the catheter housing 102, 202, 302, or 402 is also advantageous for retaining any residual urine present in the intermittent catheter 104, 204, 304, or 404 after its use until the intermittent-catheter assembly 100, 200, 300, or 400 can be properly disposed.

FIGS. 2, 5, 8, and 11 respectively show the intermittent-catheter assemblies 100, 200, 300, and 400 in their opened states, respectively. In the opened state, the catheter housing 102, 202, 302, or 402 is collapsed exposing the funnel 118, 218, 318, or 418 of the intermittent catheter 104, 204, 304, or 404 for removal of the intermittent catheter 104, 204, 304, or 404 from the catheter housing 102, 202, 302, or 402. Notably, the opened state of the intermittent-catheter assembly 100, 200, 300, or 400 includes that between the storage and disassembled states of the intermittent-catheter assembly 100, 200, 300, or 400.

Figure 12:
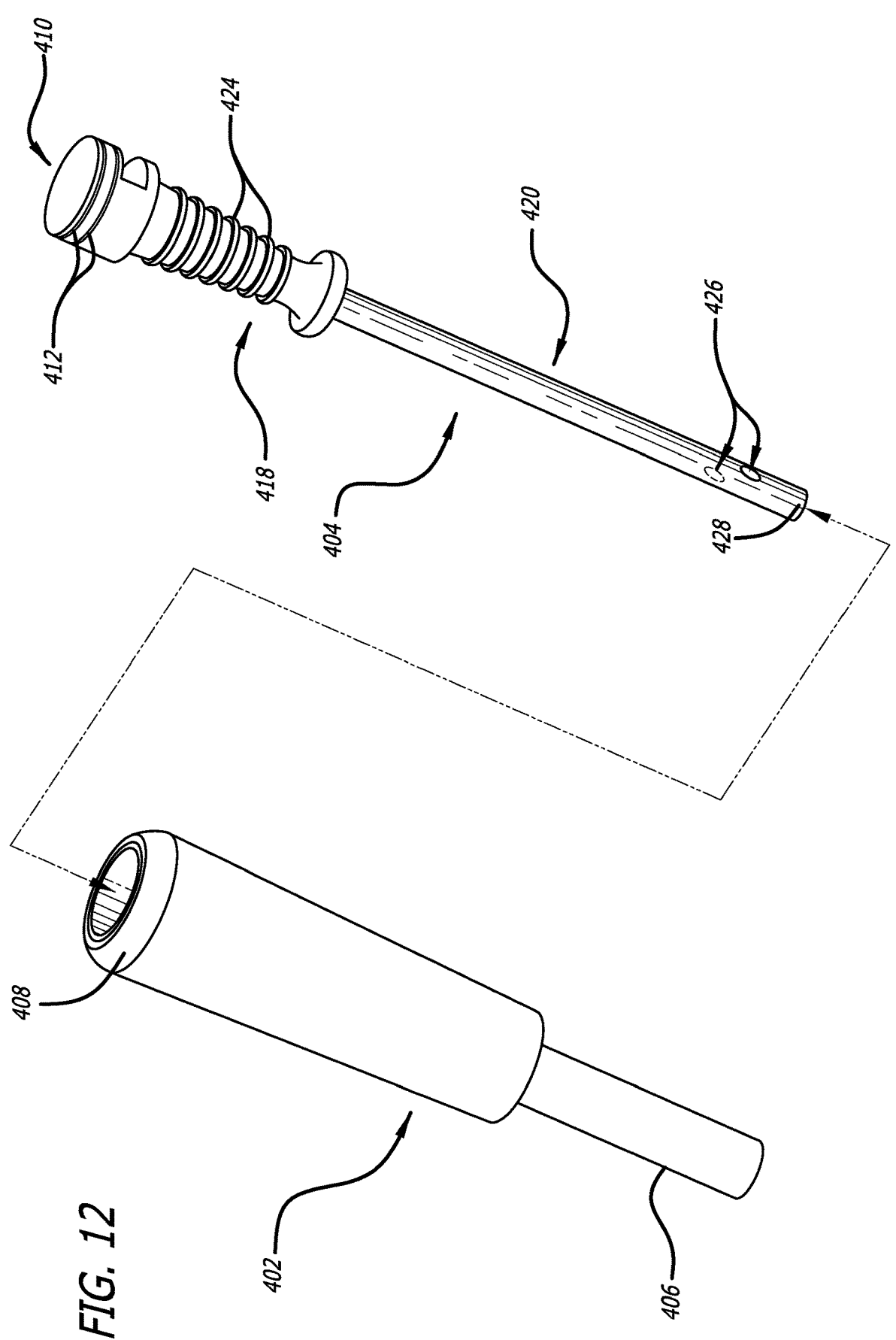
FIG. 12 illustrates the intermittent-catheter assembly of FIG. 10 in a disassembled state in accordance with some embodiments.

FIG. 12 shows the intermittent-catheter assembly 400 in its disassembled state. Indeed, the intermittent catheter 404 is fully separated from the catheter housing 402.

Catheter Housings

FIGS. 1 and 2 illustrate the catheter housing 102 of the intermittent-catheter assembly 100, FIGS. 4 and 5 illustrate the catheter housing 202 of the intermittent-catheter assembly 200, and FIGS. 7 and 8 illustrate the catheter housing 302 of the intermittent-catheter assembly 300.

While each catheter housing of the catheter housings 102, 202, and 302 features unique features as set forth below, each catheter housing of the foregoing catheter housings includes an inner sleeve 106, 206, or 306 and an outer sleeve 108, 208, or 308 slidably mounted over the inner sleeve 106, 206, or 306. Indeed, with such a configuration, the catheter housing 102, 202, or 302 is configured to collapse when a distal end of the inner sleeve 106, 206, or 306 is held against a surface S (e.g., a surface in an immediate environment such as a surface of a toilet or sink in a bathroom, a knee or thigh of a user, etc.) and the outer sleeve 108, 208, or 308 is moved toward the surface S. (See FIGS. 1, 4, and 7.) When collapsed, the catheter housing 102, 202, or 302 exposes the funnel 118, 218, or 318 of the intermittent catheter 104, 204, or 304 for removal of the intermittent catheter 104, 204, or 304 from the catheter housing 102, 202, or 302.

As shown in FIG. 2, the catheter housing 102 including the inner sleeve 106 thereof is configured to seal around the cap 110 coupled to the funnel 118 of the intermittent catheter 104. Indeed, as set forth below, the cap 110 includes the one-or-more ridges 112 (e.g., one or more annular seals) for the inner sleeve 106 to seal around.

As shown in FIG. 5, the catheter housing 202 including the inner sleeve 206 thereof is configured with a cap 210 to seal the intermittent catheter 204 in the catheter housing 202. Indeed, the cap 210 includes an annular seal 212 around a perimeter of the cap 210 (e.g., an 'O'-ring disposed in an annular groove around the perimeter of the cap 210) to seal the intermittent catheter 204 in the catheter housing 202. The cap 210 is coupled to the inner sleeve 206 by way of a pair of extension arms 214 extending from the cap 210. While not shown, the extension arms 214 can include a corresponding pair of inwardly protruding posts about end portions of the extension arms 214. The pair of posts can be disposed in a pair of outwardly opening sockets in the inner sleeve 206. Such a cap is configured to pivot to one side or another side of the intermittent-catheter assembly 200 for removal of the intermittent catheter 204 from the catheter housing 202.

Like that shown in FIG. 2, FIG. 8 shows the catheter housing 302 including the inner sleeve 306 thereof configured to seal around the cap 310 integrated into the end portion of the funnel 318 of the intermittent catheter 304. Indeed, as set forth below, the cap 310 includes the one-or-more ridges 312 (e.g., one or more annular seals) for the inner sleeve 306 to seal around.

FIG. 12 illustrates the catheter housing 402 of the intermittent-catheter assembly 400.

Different than the catheter housing 102, 202, or 302, the catheter housing 402 includes an outer sleeve 408 and a collapsible outer cover 406 coupled to the outer sleeve 408.

The outer cover 406 is configured to collapse when a distal end of the intermittent-catheter assembly 400 is held against the surface S (e.g., a surface in an immediate environment such as a surface of a toilet or sink in a bathroom, a knee or thigh of a user, etc.) and the outer sleeve 408 is moved toward the surface S. Upon collapse of the outer cover 406, the funnel 418 of the intermittent catheter 404 set forth below becomes exposed for removal of the intermittent catheter 404 from the catheter housing 402.

The outer sleeve 408 includes an inner surface including a plurality of seals 416 (e.g., 'O'-rings) configured to secure the intermittent catheter 404 in the catheter housing 402 in the storage state of the intermittent-catheter assembly 400. By securing the intermittent catheter 404 in the catheter housing 402, the seals 416 also maintain sterility of the intermittent catheter 404 prior to use of the intermittent catheter 404. In addition, the seals 416 are configured to prevent urine leakage from the intermittent-catheter assembly 400 in the storage state of the intermittent-catheter assembly 400 after use of the intermittent catheter 404.

It should be understood that while certain embodiments of the catheter housing such as the catheter housing 202 or 402 include one or more seals (e.g., the annular seal 212 of the cap 210, the seals 416, etc.) and certain embodiments of the intermittent catheter such as the intermittent catheter 104 or 304 set forth below include the one-or-more ridges 112 or 312 (e.g., one or more annular seals for the cap 110 or 310, etc.), embodiments of the intermittent-catheter assemblies 100, 200, 300, and 400 can be configured to utilize any sealing configuration set for the herein for sealing the intermittent catheter 104, 204, 304, or 404 in the catheter housing 102, 202, 302, or 402 in the storage state thereof.

Intermittent Catheters

Figures 13, 14:
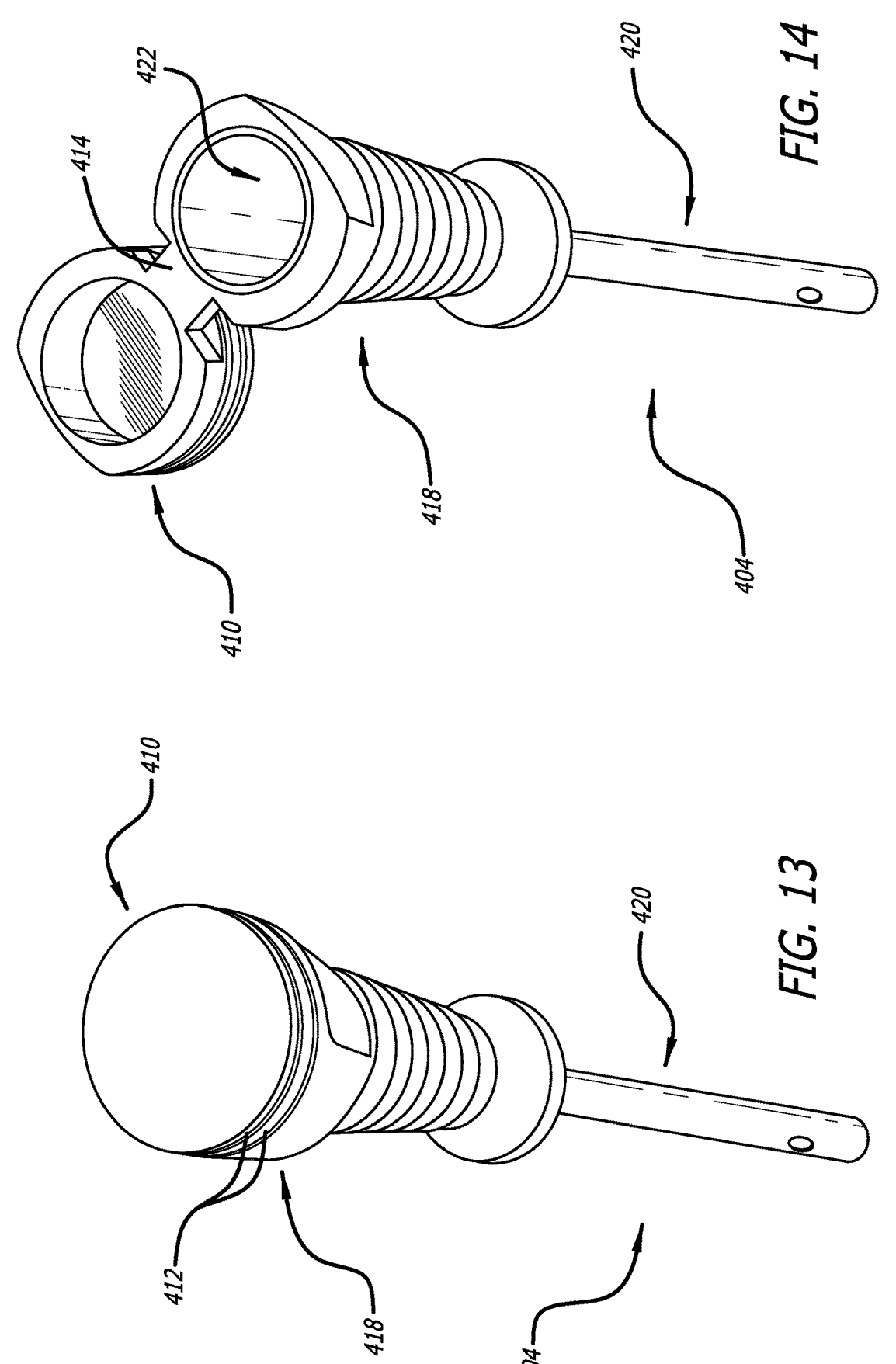
FIG. 13 illustrates an intermittent catheter of the intermittent-catheter assembly of FIG. 10 with a cap capping a funnel of the intermittent catheter in accordance in accordance with some embodiments.
FIG. 14 illustrates the intermittent catheter of the intermittent-catheter assembly of FIG. 10 without the cap capping the funnel of the intermittent catheter in accordance in accordance with some embodiments.

FIG. 3 illustrates the intermittent catheter 104 of the intermittent-catheter assembly 100, FIG. 6 illustrates the intermittent catheter 204 of the intermittent-catheter assembly 200, FIG. 9 illustrates the intermittent catheter 304 of the intermittent-catheter assembly 300, and FIGS. 12-14 illustrate the intermittent catheter 404 of the intermittent-catheter assembly 400.

While each intermittent catheter of the intermittent catheters 104, 204, 304, and 404, features unique features as set forth below, each intermittent catheter of the foregoing intermittent catheters includes a funnel and a catheter tube coupled to the funnel. Indeed, the intermittent catheter 104, 204, 304, and 404 includes a funnel 118, 218, 318, or 418 and a catheter tube 120, 220, 320, or 420 coupled to the funnel 118, 218, 318, or 418. Notably, each intermittent catheter of the intermittent catheters 104, 204, 304, and 404 is a female intermittent catheter but need not be limited thereto. Indeed, each intermittent catheter of the intermittent catheters 104, 204, 304, and 404 can alternatively be a male intermittent catheter provided the catheter housings 102, 202, 302, and 402 are modified to accommodate such catheters.

The funnel 118, 218, 318, or 418 includes a funnel opening 122, 222, 322, or 422 in a proximal end of the funnel 118, 218, 318, or 418 opposite the catheter tube 120, 220, 320, or 420 as well as a plurality of ridges 124, 224, 324, or 424 integrated into an outer surface of the funnel 118, 218, 318, or 418. The ridges 124, 224, 324, or 424 can be circumferential ridges configured for gripping the funnel 118, 218, 318, or 418 as a handle while removing the intermittent catheter 104, 204, 304, or 404 from the catheter housing 102, 202, 302, or 402 or voiding urine through the funnel opening.

The catheter tube 120, 220, 320, or 420 includes a plurality of eyelets 126, 226, 326, or 426 proximate a catheter tip 128, 228, 328, or 428. The eyelets 126, 226, 326, or 426 are in fluid communication with the funnel opening 122, 222, 322, or 422.

As shown in FIGS. 3 and 12-14, the intermittent catheter 104 or 404 can include a cap 110 or 410 configured to cap the funnel opening 122 or 422 when not actively voiding urine or preparing void urine such as in at least the storage state of the intermittent-catheter assembly 100 or 400. FIGS. 13 and 14 respectively illustrate the intermittent catheter 404 with and without the cap 410 capping the funnel opening 422 of the intermittent catheter 400. It should be understood that the intermittent catheter 104 likewise includes such states with and without the cap 110 capping the funnel opening 122 of the intermittent catheter 100. The cap 110 or 410 is coupled to the funnel 118 or 418 by a living hinge 114 or 414. The cap 110 or 410, the living hinge 114 or 414, and the funnel 118 or 418 can be molded together making each portion of the cap 110 or 410, the living hinge 114 or 414, and the funnel 118 or 418 portions an integral funnel piece.

As shown in FIG. 9, the intermittent catheter 304 can include a cap 310 integrated into an end portion of the funnel 318 opposite the catheter tube 320. With such an integrated cap, the funnel opening 322 opens in a side of the funnel 318.

As shown in FIG. 6, the intermittent catheter 204 need not include a cap of any kind when paired with the catheter housing 202, which catheter housing 202 includes the cap 210.

Notably, the cap 110, 310, or 410 can include one or more ridges 112, 312, or 412. The one-or-more ridges 112, 312, or 412 can be circumferential ridges configured for gripping the cap 110, 310, or 410 while uncapping the funnel opening 122, 322, or 422 of the funnel 118, 318, or 418. In addition, such ridges can be complementary to, for example, the seals 416 of the outer sleeve 408 of the catheter housing 402. Indeed, the one-or-more ridges 112, 312, or 412 can be one or more annular seals around a perimeter of the cap 110, 310, or 410 (e.g., one or more 'O'-rings disposed in one or more annular grooves around the perimeter of the cap 110, 310, or 410) configured to seal the intermittent catheter 104, 304, or 404 in the catheter housing 102, 302, or 402. Thus, the one-or-more ridges 112, 312, or 412 when combined with, for example, the seals 416 of the outer sleeve 408 can doubly secure the intermittent catheter 104, 304, or 404 in the catheter housing 102, 302, or 402 and doubly maintain the sterility of the intermittent catheter 104, 304, or 404 prior to use of the intermittent catheter 104, 304, or 404.

Lubricant

The intermittent-catheter assembly 100, 200, 300, or 400 can further include, in some embodiments, a lubricant. When present, the lubricant is disposed in either the inner sleeve 106, 206, or 306 between the inner sleeve 106, 206, or 306 and the catheter tube 120, 220, or 320 or in the outer cover 406 between the outer cover 406 and the catheter tube 420 in the storage state of the corresponding intermittent-catheter assembly 100, 200, 300, or 400.

Such a lubricant can include, but is not limited to, a mixture of glycerin (e.g., 60.3-73.7 wt. %), water (e.g., 28.0-36.0 wt. %), polyacrylic acid (e.g., 0.62-0.75 wt. %), propylene glycol (e.g., 0.45-0.55 wt. %), and sodium polyacrylate (e.g., 0.31-0.38 wt. %) such as that found in Lubrajel® RR-CG (Guardian Laboratories, Hauppauge, NY) disposed over a hydrophilic coating such as a silicone-based hydrophilic coating or a polyvinylpyrrolidone ("PVP")-based coating. Such a lubricant encapsulates water molecules in a matrix that activates the hydrophilic coating.

Methods

Methods of the intermittent-catheter assemblies 100, 200, 300, and 400 include methods of using the foregoing catheter assemblies. For example, a method of using the intermittent-catheter assembly 100, 200, 300, or 400 includes one or more steps selected from an assembly-obtaining step, an assembly-transitioning step, and a first catheter-removing step.

The assembly-obtaining step includes obtaining the intermittent-catheter assembly 100, 200, 300, or 400 in the storage state thereof. As set forth above, the intermittent-catheter assembly 100, 200, 300, or 400 includes the intermittent catheter 104, 204, 304, or 404 disposed in the catheter housing 102, 202, 302, or 402.

The assembly-transitioning step includes transitioning the intermittent-catheter assembly 100, 200, 300, or 400 into the opened state thereof. The assembly-transitioning step includes a sleeve-grasping step, an assembly-holding step, and a sleeve-moving step for transitioning the intermittent-catheter assembly 100, 200, 300, or 400 into the opened state thereof. The sleeve-grasping step includes grasping the outer sleeve 108, 208, 308, or 408 of the catheter housing 102, 202, 302, or 402. The assembly-holding step includes holding the distal end of the intermittent-catheter assembly 100, 200, 300, or 400 against the surface S' (e.g., the surface S of FIG. 1, 4, 7, or 11) by the outer sleeve 108, 208, 308, or 408. The sleeve-moving step includes moving the outer sleeve 108, 208, 308, or 408 toward the surface S to expose the funnel 118, 218, 318, or 418 of the intermittent catheter 104, 204, 304, or 404 (e.g., by popping the funnel 118, 218, 318, or 418 of the intermittent catheter 104, 204, 304, or 404 out of the outer sleeve 108, 208, 308, or 408). However, the sleeve-moving step can vary in accordance with the intermittent-catheter assembly 100, 200, 300, or 400 as set forth below.

The sleeve-moving step includes sliding the outer sleeve 108 or 208 over the inner sleeve 106 or 206 of the catheter housing 102 or 202 when the outer sleeve 108 or 208 is mounted over the inner sleeve 106 or 206 as in the catheter assemblies 100 and 200. Such a sleeve-moving step is accompanied by a first or second uncapping step. The first uncapping step includes uncapping the cap 110 capping the funnel opening 122 in the proximal end of the funnel 118. As set forth above, the cap 110 is coupled to the funnel 118 by the living hinge 114. The second uncapping step includes uncapping the cap 210 capping the funnel opening 222 in the proximal end of the funnel 218 by pivoting the cap 210 to one side or another side of the intermittent-catheter assembly 200. As set forth above, the cap 210 is coupled to the inner sleeve 206 by the pair of extension arms 214 extending from the cap 210. Whether the first or second uncapping step is performed, it is preferentially performed before the first catheter-inserting step set forth below.

The sleeve-moving step includes sliding the outer sleeve 308 over the inner sleeve 306 of the catheter housing 302 when the outer sleeve 308 is mounted over the inner sleeve 306 as in the catheter assembly 300. In this case, however, the sleeve-moving step includes exposing the funnel opening 322 in the side of the funnel 318. Such a sleeve-moving step need not be accompanied by a separate uncapping step because the sleeve-moving step effectively includes the uncapping step.

The sleeve-moving step includes collapsing the collapsible outer cover 406 of the catheter housing 402 when the outer sleeve 408 is coupled to the outer cover 406. Such a sleeve-moving step is accompanied by the first uncapping step. Again, the first uncapping step includes uncapping the cap 410 capping the funnel opening 422. As set forth above, the cap 410 is coupled to the funnel 418 by the living hinge 414. The first uncapping step is preferentially performed before the first catheter-inserting step set forth below.

The first catheter-removing step includes removing the intermittent catheter 104, 204, 304, or 404 from the catheter housing 102, 202, 302, or 402 by the funnel 118, 218, 318, or 418 of the intermittent catheter 104, 204, 304, or 404.

The method further includes a first catheter-inserting step and a urine-voiding step. The first catheter-inserting step includes inserting the catheter tube 120, 220, 320, or 420 of the intermittent catheter 104, 204, 304, or 404 into a urethra. The urine-voiding step includes voiding urine from a bladder.

The method further includes a second catheter-removing step and a second catheter-inserting step. The second catheter-removing step includes removing the catheter tube 120, 220, 320, or 420 from the urethra after the urine-voiding step. The second catheter-inserting step includes inserting the intermittent catheter 104, 204, 304, or 404 into the catheter housing 102, 202, 302, or 402. Optionally, the second catheter-inserting step is performed concomitantly with a capping step of capping the funnel opening 122, 222, 322, or 422 of the funnel 118, 218, 318, or 418. The second catheter-inserting step with the optional capping step seals the intermittent catheter 104, 204, 304, or 404 in the catheter housing 102, 202, 302, or 402 and prevents residual urine leakage from the intermittent-catheter assembly 100, 200, 300, or 400 in the storage state of the intermittent-catheter assembly 100, 200, 300, or 400.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An intermittent-catheter assembly, comprising:
   a collapsible catheter housing including:
      an inner sleeve; and an outer sleeve slidably mounted over the inner sleeve; and an intermittent catheter including:

a funnel having a funnel opening for voiding urine;

a cap configured to cap the funnel opening of the funnel, the cap coupled to the funnel by a living hinge; and a catheter tube coupled to the funnel, the intermittent-catheter assembly having:

a storage state in which the intermittent catheter is sealed within the collapsible catheter housing; and an opened state in which the collapsible catheter housing is collapsed exposing the funnel of the intermittent catheter for removal of the intermittent catheter from the collapsible catheter housing.

2. The intermittent-catheter assembly of claim 1, wherein the funnel opening opens in a proximal end of the funnel opposite the catheter tube.

3. The intermittent-catheter assembly of claim 1, wherein the cap includes an annular seal around a perimeter of the cap.

4. The intermittent-catheter assembly of claim 3, wherein the annular seal is an 'O'-ring disposed in an annular groove around the perimeter of the cap.

5. The intermittent-catheter assembly of claim 1, further comprising a lubricant disposed in the inner sleeve between the inner sleeve and the catheter tube in the storage state of the intermittent-catheter assembly.

6. The intermittent-catheter assembly of claim 1, wherein the collapsible catheter housing is configured to collapse when a distal end of the inner sleeve is held against a surface and the outer sleeve is moved toward the surface, thereby exposing the funnel of the intermittent catheter for removal of the intermittent catheter from the collapsible catheter housing.

7. The intermittent-catheter assembly of claim 1, wherein the funnel includes a plurality of ridges integrated into an outer surface of the funnel, the plurality of ridges configured for gripping the funnel as a handle while removing the intermittent catheter from the collapsible catheter housing for voiding urine.

8. The intermittent-catheter assembly of claim 1, wherein the catheter tube includes a plurality of eyelets proximate a catheter tip, the plurality of eyelets in fluid communication with the funnel opening.

9. An intermittent-catheter assembly, comprising:

a collapsible catheter housing including:

an outer sleeve; and a collapsible outer cover coupled to the outer sleeve; and an intermittent catheter including:

a funnel;

a cap configured to cap a proximal opening of the funnel, the cap coupled to the funnel by a living hinge; and a catheter tube coupled to the funnel, the intermittent catheter disposed in the collapsible catheter housing in a storage state of the intermittent-catheter assembly.

10. The intermittent-catheter assembly of claim 9, wherein an entirety of the funnel is disposed in the outer sleeve and a majority of the catheter tube is disposed in the collapsible outer cover in the storage state of the intermittent-catheter assembly.

11. The intermittent-catheter assembly of claim 9, further comprising a lubricant disposed in the outer sleeve between the outer sleeve and the catheter tube in the storage state of the intermittent-catheter assembly.

12. The intermittent-catheter assembly of claim 9, wherein the collapsible outer cover is configured to collapse when a distal end of the intermittent-catheter assembly is held against a surface and the outer sleeve is moved toward the surface, thereby exposing the funnel of the intermittent catheter for removal of the intermittent catheter from the collapsible catheter housing.

13. The intermittent-catheter assembly of claim 9, wherein the funnel includes a plurality of ridges integrated into an outer surface of the funnel, the plurality of ridges configured for gripping the funnel as a handle while removing the intermittent catheter from the collapsible catheter housing for voiding urine.

14. The intermittent-catheter assembly of claim 9, wherein the cap is configured to cap the funnel when not actively voiding urine.

15. The intermittent-catheter assembly of claim 9, wherein the catheter tube includes a plurality of eyelets proximate a catheter tip, the plurality of eyelets in fluid communication with the proximal opening of the funnel.

16. The intermittent-catheter assembly of claim 9, wherein an inner surface of the outer sleeve includes a plurality of seals configured to secure the intermittent catheter in the collapsible catheter housing in the storage state of the intermittent-catheter assembly, thereby maintaining sterility of the intermittent catheter prior to use of the intermittent catheter.

17. The intermittent-catheter assembly of claim 16, wherein the plurality of seals are configured to prevent urine leakage from the intermittent-catheter assembly in the storage state of the intermittent-catheter assembly after use of the intermittent catheter.

18. The intermittent-catheter assembly of claim 16, wherein the plurality of seals are 'O'-rings.

* * * * *